United States Patent [19]

Barchfeld et al.

[11] Patent Number: 5,709,879
[45] Date of Patent: Jan. 20, 1998

[54] VACCINE COMPOSITIONS CONTAINING LIPOSOMES

[75] Inventors: Gail L. Barchfeld, Hayward; Gary Ott, Oakland; Gary A. Van Nest, El Sobrante, all of Calif.

[73] Assignee: Chiron Corporation, Emeryville, Calif.

[21] Appl. No.: 469,444

[22] Filed: Jun. 6, 1995

Related U.S. Application Data

[63] Continuation of Ser. No. 308,622, Sep. 19, 1994, abandoned, which is a continuation of Ser. No. 154,160, Nov. 18, 1993, abandoned, which is a continuation of Ser. No. 722,862, Jun. 28, 1991, abandoned, which is a continuation-in-part of Ser. No. 546,585, Jun. 29, 1990, abandoned.

[51] Int. Cl.$^6$ ............................................. A61K 9/127
[52] U.S. Cl. .................. 424/450; 424/184.1; 424/204.1; 424/234.1; 424/812; 514/2; 514/937; 514/938
[58] Field of Search .................. 424/450, 88–93, 424/184.1, 204.1, 234.1, 278.1, 812–832, 93.1; 514/937, 938, 18, 19, 2; 436/829

[56] References Cited

U.S. PATENT DOCUMENTS

| | | | |
|---|---|---|---|
| 4,199,565 | 4/1980 | Fullerton | 424/89 |
| 4,396,630 | 8/1983 | Riedl et al. | 424/365 |
| 4,610,877 | 9/1986 | Pearson | 424/88 |
| 4,663,311 | 5/1987 | Tenu | 536/5 |
| 4,772,466 | 9/1988 | Allison | 424/88 |
| 4,975,420 | 12/1990 | Silversides | 424/88 |
| 5,019,386 | 5/1991 | Machida | 424/88 |
| 5,080,896 | 1/1992 | Visser | 424/450 |

OTHER PUBLICATIONS

Pescador et al J. Immunol. 141, 1720 (1988).

Anderson et al., "Effect of Dose & Immunization Schedule on Immune Response of Baboons to Recombinant Glycoprotein 120 of HIV-1," *J. Infectious Dis.*, (1989) 160(6):960-969.

Hilgers et al., "Combinations of Two Synthetic Adjuvants: Synergistic Effects of a Surfactant and a Polyanion on the Humoral Immune Response," *Cell. Immunology*, (1985) 92:203-209.

Zigterman et al., "Modulation of the Immune Response Against Liposomes Containing Liposoluble Immunogenic Materials," *Liposome Technology*, 2nd Ed., (©1993), (Entrapment of Drugs and Other Materials) II(11):185-195.

*Primary Examiner*—Gollamudi S. Kishore
*Attorney, Agent, or Firm*—Roberta L. Robins; Barbara G. McClung; Robert P. Blackburn

[57] ABSTRACT

A vaccine composition, comprising an antigenic substance in association with a liposome and an oil-in-water emulsion comprising a muramyl peptide, a metabolizable oil, and optionally an additional emulsifying agent. The two components of the adjuvant (i.e., the liposome/antigen component and the emulsion component) act together to produce high levels of immune response.

37 Claims, 7 Drawing Sheets

VACCINE COMPOSITIONS CONTAINING LIPOSOMES

This application is a continuation, of application Ser. No. 08/308,622, filed Sep. 19,1994 now abandoned, which is a continuation of application Ser. No. 08/154,160, filed Nov. 18, 1993, now abandoned, which is a continuation of application Ser. No. 07/722,862, filed Jun. 28, 1991, now abandoned, which is a continuation-in-part of application Ser. No. 07/546,585, filed Jun. 29, 1990, now abandoned, from which applications priority is claimed pursuant to 35 USC §120.

BACKGROUND OF THE INVENTION

1. Technical Field

This invention relates generally to vaccines and is particularly directed to techniques and compositions for increasing the efficiency of vaccines and generating neutralizing antibodies.

2. Background

Liposomes are spherical vesicles consisting of a lipid bilayer and an enclosed aqueous space that are typically formed of phospholipids in aqueous solutions. By incorporating chemical or biochemical substances in the aqueous phase of the suspension in which the liposomes are formed, liposomes can be obtained that enclose within their interior space various biologically active substances. Liposomes, which typically vary in size from about 25 nm to about 1 µm in diameter depending on how they are produced and the content of their lipid layer, therefore can be used as delivery vessels for various water-soluble substances. Since charged molecules generally do not penetrate lipid bilayers and since large molecules penetrate such layers only slowly, the liposome wall acts to insulate an organism to whom the liposomes have been administered from too rapid an effect by the enclosed material.

Liposomes have previously been used to modulate the immune response in animals by administering the liposomes with an antigen. The immune response can be modulated either for the purpose of inducing immunity in the host against a pathogen or for the purpose of producing antibodies used outside the host. For example, there is an increasing interest in improving and varying the capability of preparing antibodies to a wide variety of determinant sites for use in immunoassays and immunodirected therapy. The unique capability of antibodies to bind to a specific determinant site or chemical structure makes them peculiarly useful in directing drugs, radioisotopes, or markers to a particular site in a host. In addition, the ability of antibodies to distinguish a specific structure from similar structures has resulted in their wide use in diagnosis.

Regardless of whether one wishes monoclonal or polyclonal antibodies for use outside the host or an immune response to protect the host against a pathogen, the initial step is the immunization of a host. As will become clear below, the composition used in immunization is referred to herein as a "vaccine" regardless of whether the composition is used to protect the host or in the production of monoclonal antibodies. Usually one hyperimmunizes the host by repeated injections of the immunogen in a vaccine composition in accordance with a predetermined schedule. Adjuvants are added to potentiate the immune response. Various adjuvants include aluminum and calcium salts, emulsifying adjuvants and bacteria, e.g., mycobacteria and corynebacteria.

When monoclonal antibodies are desired, it is particularly desirable to enhance the immune response to specific ectopic sites. Since the preparation of monoclonal antibodies requires the detection of low population events, any technique which enhances the B-lymphocyte population of interest can prove to be important in the production of monoclonal antibodies. See U.S. Pat. No. 4,565,696 which describes the production of immunogens by conjugation of antigens to liposomes.

As will be described hereafter, the present invention is directed to the preparation of vaccine compositions containing liposomes. The liposomes, and various other components as will be discussed in detail below, act as adjuvants for increasing the immunogenicity of the antigens derived from or otherwise related to pathogenic agents.

Currently, the only adjuvants approved for human use in the United States are aluminum salts (alum). These adjuvants have been useful for some vaccines including hepatitis B, diphtheria, polio, rabies, and influenza, but may not be useful for others, especially if stimulation of cell-mediated immunity is required for protection. Reports indicate that alum failed to improve the effectiveness of both whooping cough and typhoid vaccines and provided only a slight improvement with adenovirus vaccines. Problems with aluminum salts include induction of granulomas at the injection site and lot-to-lot variation of alum preparations.

Complete Freund's Adjuvant (CFA) is a powerful immunostimulatory agent that has been used successfully with many antigens on an experimental basis. CFA is comprised of a mineral oil, an emulsifying agent such as Arlacel A, and killed mycobacteria such as *Mycobacterium tuberculosis*. Aqueous antigen solutions are mixed with these components to create a water-in-oil emulsion. CFA causes severe side effects, however, including pain, abscess formation, and fever, which prevent its use in either human or veterinary vaccines. The side effects are primarily due to the patient's reactions to the mycobacterial component of CFA.

Incomplete Freund's Adjuvant (IFA) is similar to CFA without the bacterial component. While not approved for use in the United States, IFA has been useful for several types of vaccines in other countries. IFA has been used successfully in humans with influenza and polio vaccines and with several animal vaccines including rabies, canine distemper, and hoof-and-mouth disease. Experiments have shown that both the oil and emulsifier used in IFA can cause tumors in mice, indicating that an alternative adjuvant would be a better choice for human use.

Muramyl dipeptide (MDP) represents the minimal unit of the mycobacterial cell wall complex that generates the adjuvant activity observed with CFA (see Ellouz et al. (1974) *Biochem. Biophys. Res. Comm.*, 59: 1317). Many synthetic analogues of MDP have been generated that exhibit a wide range of adjuvant potency and side effects (reviewed in Chedid et al. (1978) *Prog. Allergy,* 25:63). Three analogues that may be especially useful as vaccine adjuvants are threonyl derivatives of MDP (see Byars et al. (1987) *Vaccine,* 5:223), n-butyl derivatives of MDP (see Chedid et al. (1982) *Infect. and Immun.,* 35:417), and lipophilic derivatives of muramyl tripeptide (see Gisler et al. (1981) *Immunomodulations of Microbial Products and Related Synthetic Compounds,* Y. Yamamura and S. Kotani, eds., Excerpta Medica, Amsterdam, p. 167). These compounds effectively stimulate humoral and cell-mediated immunity and exhibit low levels of toxicity.

One promising lipophilic derivative of MDP is N-acetylmuramyl-L-alanyl-D-isoglutaminyl-L-alanine-2-[1,2-dipalmitoyl-sn-glycero-3-(hydroxyphosphoryloxy)] ethylamide (MTP-PE). This muramyl peptide has a phospholipid tail that allow association of the hydrophobic portion of the molecule with a lipid environment while the muramyl peptide portion associates with the aqueous environment. Thus the MTP-PE itself can act as an emulsifying agent to generate stable oil-in-water emulsions.

In the laboratories of the inventors, using experiments on mice, MTP-PE has been shown to be effective as an adjuvant in stimulating anti-HSV gD antibody titers against *Herpes simplex* virus gD antigen, and that effectiveness was vastly improved if the MTP-PE and gD were delivered in oil (IFA) rather than in aqueous solution. Since IFA is not approved for human use, other oil delivery systems were investigated for MTP-PE and antigen. An emulsion of 4% squalene with 0.008% Tween 80 and HSV gD gave very good results in the guinea pig. This formulation, MTP-PE-LO (low oil), was emulsified by passing through a hypodermic needle and was quite unstable. Nevertheless, MTP-PE-LO gave high antibody titers in the guinea pig and good protection in a HSV challenge of immunized guinea pigs (see Sanchez-Pescador et al. (1988) *J. Immunology*, 141:1720–1727 and *Technological Advances in Vaccine Development* (1988) Lasky et al., eds., Alan R. Liss, Inc., p. 445–469). The MTP-PE-LO formulation was also effective in stimulating the immune response to the yeast-produced HIV envelope protein in guinea pigs. Both ELISA antibody titers and virus neutralizing antibody titers were stimulated to high levels with the MTP-PE formulation. However, when the same formulation was tested in large animals, such as goats and baboons, the compositions were not as effective. The desirability of additional adjuvant formulations for use with molecular antigens in humans and other large animals was evident from this lack of predictability.

Experiments of the present inventors then demonstrated that an adjuvant composition comprising a metabolizable oil and an emulsifying agent, wherein the oil and emulsifying agent are present in the form of an oil-in-water emulsion having oil droplets substantially all of which are less than 1 micron in diameter, is an effective adjuvant composition to increase the efficiency of vaccines. Investigations showed superiority of such adjuvant compositions over adjuvant compositions containing oil and emulsifying agents in which the oil droplets are significantly larger. These adjuvant compositions are the subject of a separate patent application (U.S. application Ser. No. 357,035, filed May 25, 1989).

Nevertheless, further improvement in adjuvant formulations is still desirable. For example, immunogenic compositions that lead to enhanced cellular immune responses as well as enhanced humoral immune responses are desirable.

SUMMARY OF THE INVENTION

Accordingly, it is an object of the present invention to improve immunogenicity of vaccines, particularly subunit vaccines.

It is also an object of the present invention to provide vaccines in which cellular as well as humoral immune responses are activated.

These and other objects of the invention have been accomplished by providing a vaccine formulation comprising two components, an antigen/liposome component and an oil-in-water emulsion. The liposomes used in some embodiments are known as fusogenic liposomes, which means that they fuse with biological membranes under appropriate conditions, as discussed below. However, fusogenic liposomes are not required. Particularly useful are compositions formed using a muramyl peptide and a metabolizable oil in the form of an oil-in-water emulsion, where the oil droplets are substantially submicron size, and a separately formed liposome/antigen component that is combined with the emulsion to form the final vaccine composition.

DESCRIPTION OF SPECIFIC EMBODIMENTS

Figure 1:
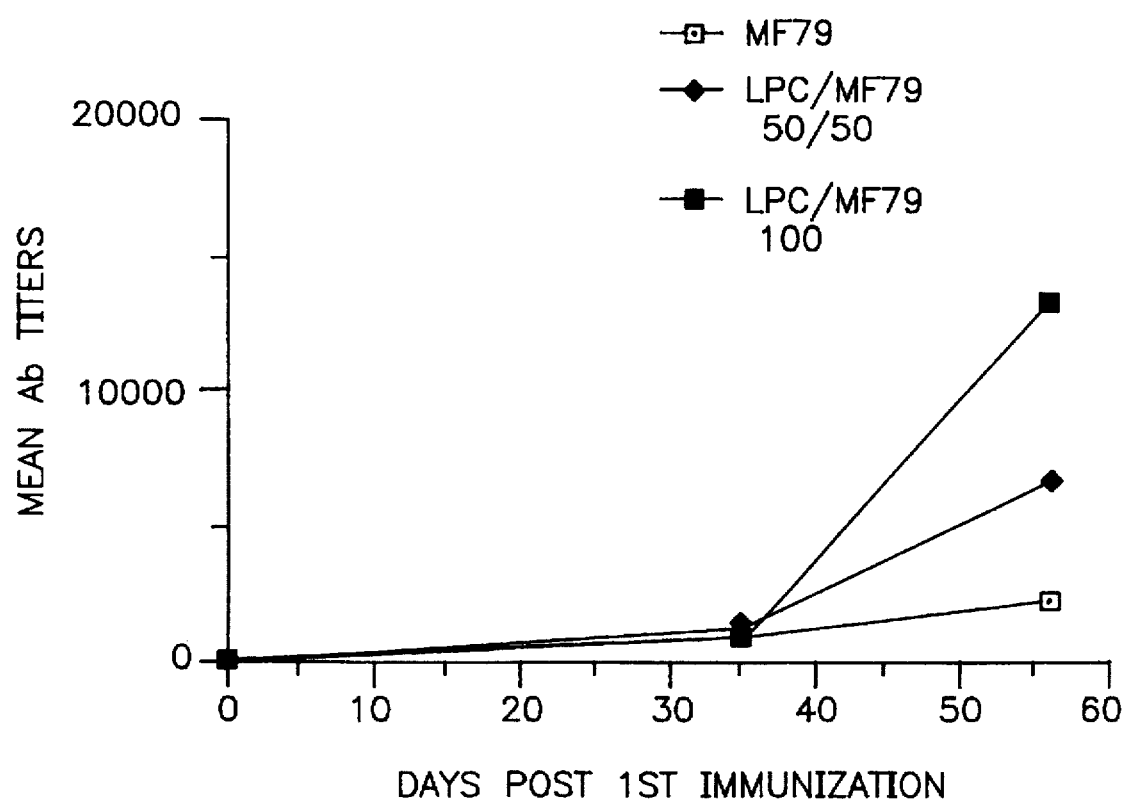
FIG. 1 is a graph showing mean antibody titers at different times after immunization with the antigen gD2 in goats using different adjuvant formulations.

The individual components of vaccine compositions of the present invention are known, but they have not been combined in the present manner. In particular, it was unexpected and surprising that such vaccine compositions would enhance the efficiency of immunogens beyond the levels previously obtained when the components were used separately.

While the individual components of the vaccine composition are described herein both generally and in some detail for preferred embodiments, all the components are well known in the art, and the terms used herein, such as liposome, muramyl peptide, metabolizable oil, and emulsifying agent, are sufficiently well known to those skilled in the art to describe and identify these components.

The liposomes used in the practice of the present invention can be prepared from a wide variety of lipid materials including phosphatidyl ethers and esters, such as phosphatidylethanolamine, phosphatidylserine, and phosphatidylcholine; glycerides, such as dioleoylglycerosuccinate; cerebrosides; gangliosides; sphingomyelin; steroids, such as cholesterol; and other lipids. See U.S. Pat. Nos. 4,235,871; 4,762,720; 4,737,323; 4,789,633; 4,861,597; and 4,873,089 for additional description of the preparation of liposomes.

The preparation of liposomes per se is not a part of the present invention, since liposomes are well known in the prior art, as indicated by the patents listed above. In general, liposomes have been made by a number of different techniques including ethanol injection, (Batzri et al., Biochem. Biophys. Acta. 298 1015 (1973)); ether infusion, (Deamer et al., *Biochem. Biophys. Acta*. 443:629 (1976) and Schieren et al., *Biochem. Biophys. Acta*. 542:137 (1978)), detergent removal, (Razin, *Biochem. Biophys. Acta*. 265:241 (1972)), solvent evaporation, (Matsumato et al., *J. Colloid Interface Sci*. 62 149 (1977)), evaporation of organic solvents from chloroform in water emulsions (REV's),(Szoka Jr. et al., *Proc. Natl. Acad. Sci. USA*, 75:4194 (1978)); extrusions of MLV's or EUV's through a nucleopore polycarbonate membrane (Olson et al., *Biochem. Biophys. Acta.* 557 9 (1979)); and freezing and thawing of phosopholipid mixtures, (Pick, *Archives of Biochem. and Biophysics*, 212:186 (1981)).

By convention, liposomes are categorized by size, and a 3-letter acronym is used to designate the type of liposome being discussed. Multilamellar vesicles are generally designated "MLV." Small unilamellar vesicles are designated "SUV," and large unilamellar vesicles are designated "LUV." These designations are sometimes followed by the chemical composition of the liposome. For a discussion of nomenclature and a summary of known types of liposomes, see Papahadjopoulos, *Ann. N.Y. Acad. Sci.*, 308:1 (1978) and *Ann. Repts. Med. Chem.*, 14:250 (1979).

A class of liposomes that has been proposed to be useful in delivering biologically active substances to cells (including substances useful as immunogens) comprises the materials known as fusogenic liposomes. These are pH-sensitive liposomes that aggregate, become destabilized, and fuse with biological membranes upon an appropriate change in physiological conditions. Such liposomes are typically made to be pH sensitive, typically acid sensitive, to take advantage of various physiological phenomena. For example, endocytosis has been shown to be the primary route by which negatively charged liposomes are internalized by mammalian cells. Endocytosis results in the liposomes being brought into the acidic environment of an endosome or lysosome. As the environment of these organelles is acidic relative to physiological conditions in the blood stream of organisms, the change in pH can be used to release the contents of the liposomes into the cellular environment. The release of antigen directly into the cytoplasm may enable class I presentation of antigen, thereby stimulating cell mediated immune response. See U.S. Pat. Nos. 4,789,633 and 4,873,089 for examples of fusogenic liposomes.

Fusogenic liposomes are generally prepared using a lipid molecule that is electrically neutral at the pH present in the blood stream of the host but which is charged at the pH present in the endosome or lysosome (typically a pH below 6.5). Examples of suitable lipids include phosphatidylethanolamine (PE) and palmitoylhomocysteine. Such fusogenic liposomes are typically composed in part of lipid molecules in which the effective cross-sectional area of the head group is smaller than the effective cross-sectional area of the hydrophobic moiety, both normal to the plane of the bilayer (i.e., PE). Further, fusogenic liposomes also contain lipid molecules capable of hydrogen bonding with the head groups of the previously described lipid molecule (e.g., oleic acid, dioleoyl glycerol succinate). When hydrogen bonding occurs, the effective surface area of the bilayer is condensed, resulting in a fusion-competent, metastable bilayer. This configuration can easily rearrange into the hexagonal II phase when closely apposed to another fusion-competent bilayer, resulting in fusion of the two membranes.

Onset of fusion can be controlled by pH, which determines the amount of interheadgroup hydrogen bonding (i.e., pH sensitive fusogenic liposomes). Alternatively, fusion can be controlled thermally; bilayers which are fusion competent must be in the lamellar α phase, or liquid crystalline state. If below $T_m$, they will be in the gel state, or lamellar β phase, and will be unable to fuse. Raising the temperature above $T_m$ will induce fusion.

It should be emphasized, however, that fusogenic liposomes are merely one embodiment of one part of the present invention and have previously been known in many forms.

As exemplary of publications describing fusogenic liposomes, see Connor et al., *Proc. Natl. Acad. Sci. U.S.A.* (1984) 81:1715–718; Schneider et al., *Proc. Natl. Acad. Sci. U.S.A.* (1980) 77:442–446; Schenkman et al., *Biochem. Biophys. Acta.* (1981) 649:633–641; Schenkman et al., *Chem. Phys. Lipids* (1981) 28:165–180; Blumenthal et al., *J. Biol. Chem.* (1983) 258:349–3415; Yatvin et al., *Science* (1980) 210:1253–1255; Duzgunes et al., *Biochemistry* (1985) 24:3091–3098; Straubinger, *Receptor-Mediated Targeting of Drugs* (Gregoriadis, Eds.) pp. 297–315, Plenum Press New York; Straubinger et al., *FEBS Lett.* (1985) 179:148–154. For general information on liposomes, their properties, and methods of preparation, see *Liposome Technology* (Gregoriadis, ed.) CRC Press, Boca Raton, Fla. (1983). For a recent general review of the use of liposomes as immunological adjuvants, including a listing of publications describing many different aspects of liposome composition, preparation, and use with antigens as immunogenic agents, see Gregoriadis, *Immunology Today* (1990) 11:89–97.

The present invention has been carried out with a number of liposome compositions, using both fusogenic liposomes and nonfusogenic liposomes. In these and other examples throughout the specification, the following abbreviations are used: PE, phosphatidyl ethanolamine; GS, dioleoyl glycerol succinate; CHOL, cholesterols OA, oleic acid; PC, phosphatidyl choline; and PS, phosphatidyl serine. One preferred fusogenic liposome composition consisted of phosphatidyl ethanolamine and dioleoyl glycerol succinate at an 8:2 molar ratio; this composition is abbreviated PE/GS. (8:2). PE/GS/CHOL (8:2:1) is also a preferred fusogenic liposome composition. Nonfusogenic liposome compositions include PC/PS (7:3) and PC/PS/CHOL (7:3:1).

The overall vaccine formulation of the invention contains, as previously mentioned, two principal components: the antigen/liposome component and the oil emulsion. Accordingly, the liposomes described herein are prepared in a first composition containing the antigen that is being used to induce the immune response, which is combined with the second (emulsion) component to form the composition of the invention.

The word antigen as used here refers to any substance (including a protein or protein-polysaccharide, protein-lipopolysaccharide, polysaccharide, lipopolysaccharide, vital subunit, or whole virus) which, when foreign to the blood stream of an animal, on gaining access to the tissue of such an animal stimulates the formation of specific antibodies and reacts specifically in vivo or in vitro with such an antibody. Moreover, the antigen stimulates the proliferation of T-lymphocytes with receptors for the antigen and can react with the lymphocytes to initiate the series of responses designated cell-mediated immunity.

A hapten is within the scope of this definition. A hapten is that portion of an antigenic molecule or antigenic complex that determines its immunological specificity. Commonly, a hapten is a peptide or polysaccharide in naturally occurring antigens. In artificial antigens it may be a low molecular weight substance such as an arsanilic acid derivative. A hapten will react specifically in vivo or in vitro with an antibody or T-lymphocyte induced by an antigenic form of the hapten (e.g., the hapten attached to an immunogenic substance). Alternative descriptors are antigenic determinant, antigenic structural grouping and haptenic grouping.

The formulation of a vaccine of the invention will employ an effective amount of an antigen. That is, there will be included an amount of antigen which, in combination with the adjuvant, will cause the subject to produce a specific and sufficient immunological response so as to impart protection to the subject from the subsequent exposure to an virus or other pathogen.

Antigens may be produced by methods known in the art or may be purchased from commercial sources. Antigens within the scope of this invention include whole inactivated virus particles, isolated virus proteins, and protein subunits (such as those produced by genetic engineering). Vaccines of the invention may be used to immunize mammals against numerous pathogens as well as to induce antibody formation for use in diagnosis.

Examples of antigens that have been incorporated in liposome-containing compositions of the invention include a recombinant protein secreted by genetically engineered Chinese hamster ovary (CHO) cells and derived from herpes simplex virus, the recombinant protein being designated HSV rgD2. This protein has the normal anchor region truncated, giving a glycolsylated protein secreted into tissue culture medium. The HSV gD2 as used in the liposomes was purified from the CHO medium to greater than 90% purity. HSV rgB2 is a fully glycosylated secreted protein produced in CHO cells similar to HSV gD2 as described above. HIV gp120 is a fully glycosylated human immunodeficiency virus protein produced in a fashion similar to that described for HSV gD2 above. HIV RT6, a recombinant form of the HIV reverse transcriptase, is produced in genetically engineered *Saccharomyces cerevisae*. This protein lacks the t terminal of the native reverse transcriptase. Both of the HIV proteins, as well as a number of different commercial influenza vaccines, have also been incorporated into liposomes for use in the practice of the present invention.

Sera 1, a recombinant form of a *Plasmodium falciparum* merozoite protein, is produced in genetically engineered *Saccharomyces cerevisae*. This protein contains only the N-terminal 262 amino acids of the native merozoite antigen. HA Taiwan, the hemagglutinin of the influenza strain A/Taiwan/1/86 (H1N1), is cultured in hen eggs by Parke-Davis for a commercial influenza vaccine. A synthetic eleven-amino acid peptide, H-Ile-Tyr-Ser-Thr-Val-Ala-Ser-Ser-Leu-Val-Leu-OH, corresponding to a T-cell epitope identified in native HSV gB2 (Hanke, T. et al. (1991): *J. of Virology* 65:1177–1186), has also be used.

A number of other antigens are specifically contemplated for use with the present composition. These include HIV-env 2-3, a genetically engineered HIV protein; various malaria viruses, such as falc. 2.3; mero; sera N; and vivax 1, 2, and 3. Cytomegalovirus (CMV) proteins, including those designated as gB and gH, are also contemplated along with various hepatitis C virus (HCV) proteins. For a more detailed description of these antigens, as well as a listing of a number of publications in which these and other antigens are described in detail, see U.S. application Ser. No. 357, 035, filed May 25, 1989. Also see the corresponding PCT application, Ser. No. PCT/US90/02954, filed May 24, 1990, and entitled "Adjuvant Formulation Comprising a Submicron Oil Droplet Emulsion."

In general, the present invention can be used with any natural or recombinant protein or subunit protein that is suitable for vaccine development as well as with peptides comprising B-cell and T-cell epitopes. Non-proteinaceous antigens (e.g., carbohydrates, glycolipids) can also be used.

No single dose designation can be assigned which will provide specific guidance for each and every antigen which may be employed in this invention. The effective amount of antigen will be a function of its inherent activity and purity as is understood in the art. Exemplary values are discussed below in a section describing relative amounts of the various components of the inventive composition.

The emulsion component of the present invention comprises a muramyl peptide and a metabolizable oil in an oil-in-water emulsion. The suspended oil droplets may be of any suitable size and need not be substantially submicron for use in increasing the efficiency of vaccines, although submicron oil droplets are preferred, as described below. The muramyl peptide functions as an immunostimulant in the adjuvant composition and also possesses emulsifying properties so that no separate emulsifying agent is required. Nevertheless, the emulsion component of the present invention preferably include one or more additional emulsifying agents.

Any immune-response-stimulating muramyl peptide (also known as a glycopeptide) can be used in the present invention composition. A number of preferred muramyl peptides are set forth below.

Examples of the joint emulsifying agent/immunostimulating agent are the lipophilic muramyl peptides described in the two Sanchez-Pescador et al. publications cited above. These materials comprise the basic N-acetylmuramyl peptide (a hydrophilic moiety) that acts as an immunostimulating group, but also include a lipophilic moiety that provides surface-active characteristics to the resulting compound. Such compounds, as well as other types of amphipathic immunostimulating substances, act as both immunostimulating agents and emulsifying agents and are preferred in the practice of the present invention. In addition, it is also possible to practice the present invention by using a amphipathic immunostimulating substance in combination with a second immunostimulating substance that is not amphipathic. An example would be use of a lipophilic muramyl peptide in combination with an essentially unsubstituted (i.e., essentially hydrophilic) muramyl dipeptide.

The preferred immune-response-stimulating muramyl peptides of this invention are a group of compounds related to and generally derived from N-acetylmuramyl-L-alanyl-D-isoglutamine, which was determined by Ellouz et al. (1974) *Biochem. & Biophys. Res. Comm.*, 59:1317, to be the smallest effective unit possessing immunological adjuvant activity in *M. tuberculosis*, the mycobacterial component of Freund's complete adjuvant. A number of dipeptide- and polypeptide-substituted muramic acid derivatives were subsequently developed and found to have immunostimulating activity.

Though these muramyl peptides are a diverse group of compounds, they can be generally represented by Formula I below:

$$\text{(I)}$$

(structure of muramyl peptide with ROCH$_2$, pyran ring, OR, NHCOR, R, and peptide substituents)

wherein the pyran ring hydroxyl oxygens are substituted by hydrogen, alkyl, or acyl or the like, or may be replaced by nitrogen-based substituents, particularly the 6-position oxygen; the 2-amino group is an acyl group or some other amide; the lactyl side chain is modified, e.g., is ethyl or another two-position alkyl moiety; and the peptide function is a dipeptide or polypeptide, which may be further derivatized. Furanosyl analogs of the pyranosyl compounds also have immunopotentiating activity and are useful in this invention.

Among the muramyl peptides usable in this invention are those disaccharides and tetrasaccharides linked by meso-α, ε-diaminopimelic acid such as described in U.S. Pat. Nos. 4,235,771 and 4,186,194.

Other immune response stimulating muramyl peptides which may be used in the practice of this invention are disclosed in U.S. Pat. Nos. 4,094,971; 4,101,536; 4,153,684; 4,235,771; 4,323,559 4,327,085; 4,185,089; 4,082,736; 4,369,178; 4,314,998 4,082,735; and 4,186,194. The disclosures of muramyl peptides in these patents are incorporated herein by reference and made a part hereof as if set out in full herein. The compounds of Japanese patent documents J5 4079-2227, J5 4079-228, and J5 41206-696 are also useful in the practice of this invention.

Methods for preparing these compounds are disclosed and well-known in the art. Preparative process exemplification can be found in U.S. Pat. Nos. 4,082,736 and 4,082,735. Additionally, similar preparative processes may be found in the U.S. patents referenced in the preceding paragraph.

Preferred muramyl peptides are those having the Formula II

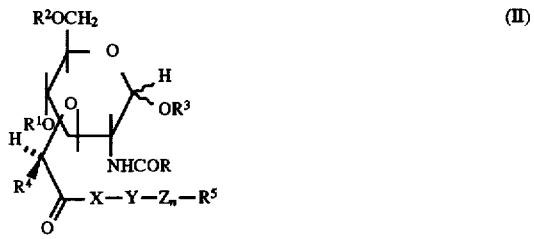

wherein

R is an unsubstituted or substituted alkyl radical containing from 1 to 22 carbon atoms, or an unsubstituted or substituted aryl radical containing from 6 to 10 carbon atoms;

$R^1$ and $R^2$ are the same or different and are hydrogen or an acyl radical containing from 1 to 22 carbon atoms;

$R^3$ is hydrogen, alkyl of 1 to 22 carbons, or aryl of 7 to 10 carbon atoms;

$R^4$ is hydrogen or alkyl of 1 to 7 carbons;

n is 0 or 1;

X and Z are independently alanyl, valyl, leucyl, isoleucyl, α-aminobutyryl, threonyl, methionyl, cysteinyl, glutamyl, glutaminyl, isoglutamyl, isoglutaminyl, aspartyl, phenylalanyl, tyrosyl, lysyl, orinthinyl, arginyl, histidyl, asparaginyl, prolyl, hydroxyprolyl, seryl, or glycyl;

$R^5$ is an optionally esterified or amidated carboxyl group of the terminal amino acid; and Y is —NHCHR$^6$CH$_2$CH$_2$CO—, wherein $R^6$ is an optionally esterified or amidated carboxyl group.

An optionally esterified or amidated carboxyl group is the carboxyl group itself or a carboxyl group esterified with a $C_1$–$C_4$ alkanol, such as methanol, ethanol, propanol, butanol, or a carbamoyl group, which, on the nitrogen atom, is unsubstituted or monosubstituted or di-substituted by $C_1$–$C_7$ alkyl, especially a $C_1$–$C_4$ alkyl, aryl, particularly phenyl, or arylalkyl, particularly benzyl. The carbamoyl group may also be substituted with an alkylidene radical such as butylidene or pentylidene radical. In addition, the carbamoyl group $R^5$ may also be substituted with a carbamoylmethyl group on the nitrogen atom.

Particularly preferred compounds are those of Formula II wherein R and $R^1$ are the same or different and are hydrogen or an acyl radical containing from 1 to 22 carbon atoms; $R^2$ is methyl; $R^3$ is hydrogen; X is L-alanyl, Y is D-isoglutaminyl, and n is 0.

A different preferred group of muramyl peptides are the compounds of Formula II wherein R and $R^1$ are hydrogen or acyl of 1 to 22 carbon atoms, $R^2$ is methyl, $R^3$ is hydrogen, $R^4$ is methyl or butyl, and X is L-valyl, E-seryl, L-alanyl, L-threonyl or L-α-aminobutyryl.

Specific examples include the following compounds:

N-acetylmuramyl-L-α-aminobutyryl-D-isoglutamine;

6-O-stearoyl-N-acetylmuramyl-L-α-aminobutyryl-D-isoglutamine;

N-acetylmuramyl-L-threonyl-D-isoglutamine;

N-acetylmuramyl-L-valyl-D-isoglutamine;

N-acetylmuramyl-L-alanyl-D-glutamine n-butyl ester;

N-acetyl-desmethyl-D-muramyl-L-alanyl-D-isoglutamine;

N-acetylmuramyl-L-alanyl-D-glutamine;

N-acetylmuramyl-L-seryl-D-iosoglutamine;

N-acetyl(butylmuramyl)-L-e-aminobutyl-D-isoglutamine; and

N-acetyl(butylmuramyl)-L-alanyl-D-isoglutamine.

An effective amount of immunostimulating muramyl peptide is that amount which effects an increase in antibody titer level when administered in conjunction with an antigen over that titer level observed when the muramyl peptide has not been co-administered. As can be appreciated, each muramyl peptide may have an effective dose range that may differ from other muramyl peptides. Therefore, a single dose range cannot be prescribed which will have a precise fit for each possible muramyl peptide within the scope of this invention. However, as a general rule, the muramyl peptide will preferably be present in the vaccine in an amount of between 0.001 and 5% (w/v). A more preferred amount is 0.01 to 3% (w/v).

Most of the immunostimulating muramyl peptides discussed above are essentially hydrophilic compounds. Accordingly, they are intended for use with a separate emulsifying agent (which can be, as discussed above, also an immunostimulating agent). In some cases, the above-described compounds have a lipophilic character, such as the compounds comprising fatty acid substituents and/or aryl substituents on the sugar moiety, particularly those containing one or more acyl radicals containing from 14 to 22 carbon atoms, particularly those containing more than 1 such acyl substituent. However, it is also possible to achieve lipophilic character in a muramyl peptide by providing a lipid moiety linked through the carboxylate group or side chains of the peptide moiety. In particular, compounds having one or more lipid groups joined to the peptide moiety through the terminal carboxylate group represent a preferred group of compounds. This linkage can readily be provided either directly, such as by forming an ester linkage between the terminal carboxylate and a fatty acid alcohol containing from 14 to 22 carbon atoms, or by using a bifunctional linking group, such as ethanolamine, to link the carboxylate through either an ester or amide linkage to a lipid. Particularly preferred in this embodiment of the invention are phospholipids, as the phosphate groups provide a readily linkable functional group. Diacylphospho-glycerides provide one such readily linkable phospho-lipid. Phosphatidyl ethanolamine, a readily linkable, naturally occurring compound, can be easily linked to the terminal carboxylate of the peptide moiety through an amide bond. Other lipids include acylglycerols, phosphatidyl choline, phosphatidyl serine, phosphatidyl inositol, phosphatidyl glycerol, cardiolipin, and sphingomyelin.

A number of preferred amphipathic immuno-stimulating peptides are those having Formula III below:

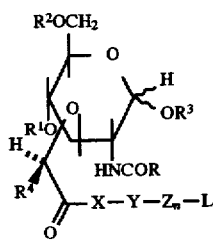

(III)

wherein R, $R^1$—$R^4$, X, Y, Z and n have previously described meanings. L represents a lipid moiety, such as the lipid moieties described herein.

In summary, the muramic acid moiety and the peptide moiety of the molecule together provide a hydrophilic moiety. A lipophilic moiety is also present in the molecule, lipophilicity generally being provided by a long-chain hydrocarbon group, typically present in the form of a fatty acid. The fatty acid or other hydrocarbon-containing radical can be attached to a hydroxyl group of the sugar or can be linked to the peptide portion of the molecule either directly, such as by reacting a fatty acid with a free amino group present in the peptide moiety, or through a linking group, such as a hydroxyalkylamine that forms a link between a carboxylic acid group of the peptide through amide bond formation and a functional group in a lipid, such as a phosphate group. Phospholipid moieties are particularly preferred for use in forming lipophilic muramyl peptides. A group of preferred compounds include muramyl dipeptides and tripeptides linked to a phospholipid moiety through a hydroxyalklamine moiety. An example, and a particularly preferred compound, is N-acetylmuramyl-L-alanyl-D-isoglutaminyl-L-alanine-2-[1,2-dipalmitoyl-sn-glycero-3-(hydroxy-phosphoryloxy)]ethylamide (abbreviated MTP-PE), manufactured by Ciba-Geigy, Ltd., Basel, Switzerland.

Another component used in the present invention is a metabolizable, non-toxic oil, preferably one of 6 to 30 carbon atoms including, but not limited to, alkanes, alkenes, alkynes, and their corresponding acids and alcohols, the ethers and esters thereof, and mixtures thereof. The oil may be any vegetable oil, fish oil, animal oil or synthetically prepared oil which can be metabolized by the body of the subject to which the adjuvant will be administered and which is not toxic to the subject. The subject is an animal, typically a mammal, and preferably a human. Mineral oil and similar toxic petroleum distillate oils are expressly excluded from this invention.

The oil component of this invention may be any long chain alkane, alkene, or alkyne, or an acid or alcohol derivative thereof either as the free acid, its salt or an ester such as a mono-, di-, or triester, such as the triglycerides and esters of 1,2-propanediol or similar poly-hydroxy alcohols. Alcohols may be acylated employing a mono- or polyfunctional acid, for example acetic acid, propanic acid, citric acid or the like. Ethers derived from long chain alcohols which are oils and meet the other criteria set forth herein may also be used.

The individual alkane, alkene or alkyne moiety and its acid or alcohol derivatives generally will have 6–30 carbon atoms. The moiety may have a straight or branched chain structure. It may be fully saturated or have one or more double or triple bonds. Where mono or poly ester- or ether-based oils are employed, the limitation of 6–30 carbons applies to the individual fatty acid or fatty alcohol moieties, not the total carbon count.

Any metabolizable oil may be used herein, including artificial oils, but those oils derived from an animal, fish, or vegetable source are preferred. It is essential that the oil be metabolized by the host to which it is administered; otherwise the oil component may cause abscesses, granulomas or even carcinomas, or, when used in veterinary practice, may make the meat of vaccinated birds and animals unacceptable for human consumption due to the deleterious effect the unmetabolized oil may have on the consumer.

Sources for vegetable oils include nuts, seeds and grains. Peanut oil, soybean oil, coconut oil, and olive oil, the most commonly available, exemplify the nut oils. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used.

The technology for obtaining vegetable oils is well developed and well known. The compositions of these and other similar oils may be found in, for example, the Merck Index and source materials on foods, nutrition and food technology.

The 6–10 carbon fatty acid esters of glycerol and 1,2-propanediol, while not occurring naturally in seed oils, may be prepared by hydrolysis, separation and esterification of the appropriate materials starting from the nut and seed oils. These products are commercially available under the name NEOBEE® from PVO International, Inc., Chemical Specialties Division, 416 Division Street, Boongon, N.J. and others.

Oils from many animal sources may be employed in the adjuvants and vaccines of this invention. Animal oils and fats are usually solids at physiological temperatures because they are triglycerides and have a higher degree of saturation than oils from fish or vegetables. However, fatty acids are obtainable from animal fats by partial or complete triglyceride saponification which provides the free fatty acids. Fats and oils from mammalian milk are metabolizable and may therefore be used in the practice of this invention. The procedures for separation, purification, saponification and other means necessary for obtaining pure oils from animal sources are well known in the art.

Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a particularly preferred oil. Fish oils, including squalane and squalene, are readily available from commercial sources or may be obtained by methods known in the art.

The oil component of these adjuvants and vaccine formulations will be present in an amount from 0.5% to 15% by volume preferably in an amount of 1% to 12%. It is most preferred to use from 1% to 4% oil.

The aqueous portion of these adjuvant compositions is generally buffered saline or, in some preferred embodiments, unadulterated water. Because these compositions are intended for parenteral administration, it is preferable to make up final buffered solutions used as vaccines so that the tonicity, i.e., osmolality, is essentially the same as that of normal physiological fluids in order to prevent post-administration swelling or rapid absorption of the composition because of differential ion concentrations between the composition and physiological fluids. It is also preferable to buffer the saline in order to maintain a pH compatible with normal physiological conditions. Also, in certain instances, it may be necessary to maintain the pH at a particular level in order to insure the stability of certain composition components such as the glycopeptides.

Any physiologically acceptable buffer may be used herein, but phosphate buffers are preferred. Other acceptable buffers such as citrate, acetate, tris, bicarbonate, carbonate, or the like may be used as substitutes for phosphate buffers. The pH of the aqueous component will preferably be between 6.0 and 8.0.

However, if the adjuvant is prepared as a submicron oil-in-water emulsion, unadulterated water is preferred as the aqueous component of the emulsion during emulsion formation. Increasing the salt concentration makes it more difficult to achieve the desired small droplet size. When the final vaccine formulation is prepared from the adjuvant, the antigenic material can be added in a buffer at an appropriate osmolality to provide the desired vaccine composition.

The quantity of the aqueous component employed in these compositions will be that amount necessary to bring the value of the composition to unity. That is, a quantity of aqueous component sufficient to make 100% will be mixed with the other components listed above in order to bring the compositions to volume. A substantial number of emulsifying and suspending agents are generally used in the pharmaceutical sciences. These include naturally derived materials such as gums from trees, vegetable protein, sugar-based polymers such as alginates and cellulose, and the like. Certain oxypolymers or polymers having a hydroxide or other hydrophilic substituent on the carbon backbone have surfactant activity, for example, povidone, polyvinyl alcohol, and glycol ether-based mono- and poly-functional compounds. Long-chain-fatty-acid-derived compounds form a third substantial group of emulsifying and suspending agents which could be used in this invention. Any of the foregoing surfactants are useful so long as they are non-toxic.

Specific examples of suitable emulsifying agents (also referred to as surfactants or detergents) which can be used in accordance with the present invention include the following:

1. Water-soluble soaps, such as the sodium, potassium, ammonium and alkanol-ammonium salts of higher fatty acids ($C_{10}$–$C^{22}$), and, particularly sodium and potassium tallow and coconut soaps.

2. Anionic synthetic non-soap detergents, which can be represented by the water-soluble salts of organic sulfuric acid reaction products having in their molecular structure an alkyl radical containing from about 8 to 22 carbon atoms and a radical selected from the group consisting of sulfonic acid and sulfuric acid ester radicals. Examples of these are the sodium or potassium alkyl sulfates, derived from tallow or coconut oil; sodium or potassium alkyl benzene sulfonates; sodium alkyl glyceryl ether sulfonates; sodium coconut oil fatty acid monoglyceride sulfonates and sulfates; sodium or potassium salts of sulfuric acid esters of the reaction product of one mole or a higher fatty alcohol and about 1 to 6 moles of ethylene oxide; sodium or potassium alkyl phenol ethylene oxide ether sulfonates, with 1 to 10 units of ethylene oxide per molecule and in which the alkyl radicals contain from 8 to 12 carbon atoms; the reaction product of fatty acids esterified with isethionic acid and neutralized with sodium hydroxide; sodium or potassium salts of a fatty acid amide of a methyl tauride; and sodium and potassium salts of $SO_3$-sulfonated $C_{10}$–$C_{24}$ α-olefins.

3. Nonionic synthetic detergents made by the condensation of alkylene oxide groups with an organic hydrophobic compound. Typical hydrophobic groups include condensation products of propylene oxide with propylene glycol, alkyl phenols, condensation products of propylene oxide and ethylene diamine, aliphatic alcohols having 8 to 22 carbon atoms, and amides of fatty acids.

4. Nonionic detergents, such as amine oxides, phosphine oxides and sulfoxides, having semipolar characteristics. Specific examples of long chain tertiary amine oxides include dimethyldodecylamine oxide and bis-(2-hydroxyethyl) dodecylamine. Specific examples of phosphine oxides are found in U.S. Pat. No. 3,304,263 which issued Feb. 15, 1967, and include dimethyldodecylphosphine oxide and dimethyl-(2-hydroxydodecyl) phosphine oxide.

5. Long chain sulfoxides, including those corresponding to the formula $R_1$—SO—$R_2$ wherein $R_1$ and $R_2$ are substituted or unsubstituted alkyl radicals, the former containing from about 10 to about 28 carbon atoms, whereas $R_2$ contains from 1 to 3 carbon atoms. Specific examples of these sulfoxides include dodecyl methyl sulfoxide and 3-hydroxy tridecyl methyl sulfoxide.

6. Ampholytic synthetic detergents, such as sodium 3-dodecylaminopropionate and sodium 3-dodecylaminopropane sulfonate.

7. Zwitterionic synthetic detergents, such as 3-(N,N-dimethyl-N-hexadecylammonio) propane-1-sulfonate and 3-(N,N-dimethyl-N-hexadecylammonio)-2-hydroxypropane-1-sulfonate.

Additionally, all of the following types of emulsifying agents can be used in a composition of the present inventions (a) soaps (i.e., alkali salts) of fatty acids, rosin acids, and tall oil; (b) alkyl arene sulfonates; (c) alkyl sulfates, including surfactants with both branched-chain and straight-chain hydrophobic groups, as well as primary and secondary sulfate groups; (d) sulfates and sulfonates containing an intermediate linkage between the hydrophobic and hydrophilic groups, such as the fatty acylated methyl taurides and the sulfated fatty monoglycerides; (e) long-chain acid esters of polyethylene glycol, especially the tall oil esters; (f) polyethylene glycol ethers of alkylphenols; (g) polyethylene glycol ethers of long-chain alcohols and mercaptans; (h) fatty acyl diethanol amides; and (i) block copolymers of ethylene oxide and propylene oxide. Since surfactants can be classified in more than one manner, a number of classes of surfactants set forth in this paragraph overlap with previously described surfactant classes.

There are a number of emulsifying agents specifically designed for and commonly used in biological situations. For example, a number of biological detergents (surfactants) are listed as such by Sigma Chemical Company on pages 310–316 of its 1987 Catalog of Biochemical and Organic Compounds. Such surfactants are divided into four basic types: anionic, cationic, zwitterionic, and nonionic. Examples of anionic detergents include alginic acid, caprylic acid, cholic acid, 1-decanesulfonic acid, deoxycholic acid, 1-dodecanesulfonic acid, N-lauroylsarcosine, and taurocholic acid. Cationic detergents include dodecyltrimethylammonium bromide, benzalkonium chloride, benzyldimethylhexadecyl ammonium chloride, cetylpyridinium chloride, methylbenzethonium chloride, and 4-picoline dodecyl sulfate. Examples of zwitterionic detergents include 3-[(3-cholamidopropyl)-dimethylammonio]-1-propanesulfonate (commonly abbreviated CHAPS), 3-[(cholamidopropyl)-dimethylammonio]-2-hydroxy-1-propanesulfonate (generally abbreviated CHAPSO), N-dodecyl-N,N-dimethyl-3-ammonio-1-propanesulfonate, and lyso-α-phosphatidylcholine. Examples of nonionic detergents include decanoyl-N-methylglucamide, diethylene glycol monopentyl ether, n-dodecyl β-D-glucopyranoside, ethylene oxide condensates of fatty alcohols (e.g., sold under the trade name Lubrol), polyoxyethylene ethers of fatty acids (particularly $C_{12}$–$C_{20}$ fatty acids), polyoxyethylene sorbitan fatty acid ethers (e.g., sold under the trade name Tween), and sorbitan fatty acid ethers (e.g., sold under the trade name Span).

A particularly useful group of surfactants are the sorbitan-based non-ionic surfactants. These surfactants are prepared by dehydration of sorbitol to give 1,4-sorbitan which is then reacted with one or more equivalents of a fatty acid. The fatty-acid-substituted moiety may be further reacted with ethylene oxide to give a second group of surfactants. The fatty-acid-substituted sorbitan surfactants are made by reacting 1,4-sorbitan with a fatty acid such as lauric acid, palmitic acid, stearic acid, oleic acid, or a similar long chain fatty acid to give the 1,4-sorbitan mono-ester, 1,4-sorbitan sesquiester or 1,4-sorbitan triester. The common names for these surfactants include, for example, sorbitan monolaurate, sorbitan monopalmitate, sorbitan monestearate, sorbitan monooleate, sorbitan sesguioleate, and sorbitan trioleate. These surfactants are commercially available under the name SPAN® or ARLACEL®, usually with a letter of number designation which distinguishes between the various mono, di- and triester substituted sorbitans.

SPAN® and ARLACEL® surfactants are hydrophilic and are generally soluble or dispersible in oil. They are also soluble in most organic solvents. In water they are generally insoluble but dispersible. Generally these surfactants will have hydrophilic-lipophilic balance (HLB) number between 1.8 and 8.6. Such surfactants can be readily made by means known in the art or are commercially available from, for example, ICI America's Inc., Wilmington, Del. under the registered mark ATLAS®.

A related group of surfactants comprises polyoxyethylene sorbitan monoesters and polyoxyethylene sorbitan triesters. These materials are prepared by addition of ethylene oxide to a 1,4-sorbitan monoester or triester. The addition of polyoxyethylene converts the lipophilic sorbitan mono- or triester surfactant to a hydrophilic surfactant generally soluble or dispersible in water and soluble to varying degrees in organic liquids.

These materials, commercially available under the mark TWEEN®, are useful for preparing oil-in-water emulsions and dispersions, or for the solubilization of oils and making anhydrous ointments water-soluble or washable. The TWEEN® surfactants may be combined with a related sorbitan monoester or triester surfactants to promote emulsion stability. TWEEN® surfactants are commercially available from a number of manufacturers, for example ICI America's Inc., Wilmington, Del. under the registered mark ATLAS® surfactants.

A third group of non-ionic surfactants which could be used alone or in conjunction with SPAN®, ARLACEL® and TWEEN® surfactants are the polyoxyethylene fatty acids made by the reaction of ethylene oxide with a long-chain fatty acid. The most commonly available surfactant of this type is sold under the name MYRJ® and is a polyoxyethylene derivative of stearic acid. MYRJ® surfactants are hydrophilic and soluble or dispersible in water like TWEEN® surfactants. The MYRJ® surfactants may be blended with TWEEN® surfactants or with TWEEN®/SPAN® or ARLACEL® surfactant mixtures for use in forming emulsions. MYRJ® surfactants can be made by methods known in the art or are available commercially from ICI America's Inc.

A fourth group of polyoxyethylene-based non-ionic surfactants are the polyoxyethylene fatty acid ethers derived from lauryl, acetyl, stearyl and oleyl alcohols. These materials are prepared as above by addition of ethylene oxide to a fatty alcohol. The commercial name for these surfactants is BRIJ®. BRIJ® surfactants may be hydrophilic or lipophilic depending on the size of the polyoxyethylene moiety in the surfactant. While the preparation of these compounds is available from the art, they are also readily available from such commercial sources as ICI America's Inc.

Other non-ionic surfactants which could potentially be used in the practice of this invention include polyoxyethylene, polyol fatty acid esters, polyoxyethylene ether, polyoxypropylene fatty ethers, bee's wax derivatives containing polyoxyethylene, polyoxyethylene lanolin derivative, polyoxyethylene fatty acid glycerides, and glycerol fatty acid esters or other polyoxyethylene acid alcohol or ether derivatives of long-chain fatty acids of 12–22 carbon atoms.

As the adjuvant and the vaccine formulations of this invention are intended to be multi-phase systems, it is preferable to choose an emulsion-forming non-ionic surfactant which has an HLB value in the range of about 7 to 16. This value may be obtained through the use of a single non-ionic surfactant such as a TWEEN® surfactant or may be achieved by the use of a blend of surfactants such as with a sorbitan mono-, di- or triester based surfactant; a sorbitan ester-polyoxyethylene fatty acid; a sorbitan ester in combination with a polyoxyethylene lanolin derived surfactant; a sorbitan ester surfactant in combination with a high HLB polyoxyethylene fatty ether surfactant; or a polyethylene fatty ether surfactant or polyoxyethylene sorbitan fatty acid.

It is more preferred to use single non-ionic surfactant, most particularly a TWEEN® surfactant, as the emulsion stabilizing non-ionic surfactant in the practice of this invention. The surfactant named TWEEN® 80, otherwise known as polysorbate 80 or polyoxyethylene 20 sorbitan monooleate, is the most preferred of the foregoing surfactants.

Suitable oil-in-water emulsions can usually be effected by having the surfactant present in an amount of 0.02% to 2.5% by weight (w/w). An amount of 0.05% to 1% is preferred with 0.01 to 0.5% being especially preferred.

The manner in which oil-in-water emulsion of the invention is reached is not important to the practice of the present invention. One manner in which such an emulsion can be obtained is by use of a commercial emulsifiers, such as model number 110Y available from Microfluidics, Newton, Mass. Examples of other commercial emulsifiers include Gaulin Model 30CD (Gaulin, Inc., Everett, Mass.) and Rainnie Minlab Type 8.30H (Micro Atomizer Food and Dairy, Inc., Hudson, Wis.). These emulsifiers operate by the principle of high shear forces developed by forcing fluids through small apertures under high pressure. While the use of the present invention does not preclude use of such emulsifiers, their use is not necessary, nor preferred, to practice the present invention. If submicron oil droplets are not desired, other apparatuses that develop lower shear forces can be used (including simple passage of formulations through a syringe needle).

The size of the oil droplets can be varied by changing the ratio of detergent to oil (increasing the ratio decreases droplet size), operating pressure (increasing operating pressure decreases droplet size), temperature (increasing temperature decreases droplet size), and adding an amphipathic immunostimulating agent (adding such agents decreases droplet size). Actual droplet size will vary with the particular detergent, oil, and immunostimulating agent (if any) and with the particular operating conditions selected. Droplet size can be verified by use of sizing instruments, such as the commercial Sub-Micron Particle Analyzer (Model N4MD) manufactured by the Coulter Corporation.

The emulsion components are prepared from the ingredients described above prior to combining with the liposome/antigen component that will be used in the vaccine. The liposomes cannot be prepared in the presence of the emulsion components, because the phospholipids and other components of the liposomes would simply be incorporated into the emulsion and function as emulsifiers.

Since the emulsion component of the invention is stable, the liposome/antigen and emulsion can be combined by simple mixing, stirring, or shaking. Other techniques, such as passing a mixture of the two components rapidly through a small opening (such as a hypodermic needle) readily provides a useful vaccine composition.

The various components of the composition of the present invention can be present in a wide range of ratios. The liposome/antigen and emulsion components are typically used in a volume ratio of 1:10 to 10:1. Volume ratios of from 1:3 to 3:1 are preferred, with volume ratios of about 1:1 being preferred, as they are easy to prepare and readily discernable. However, other ratios may be more appropriate for specific purposes, such as when a particular antigen is both difficult to incorporate into a liposome and has a low immunogenicity, in which case a higher relative amount of the antigen component is required.

Liposomes are generally prepared at about 1 to 100 mg lipid per ml of lipid suspension for a final concentration of about 0.5 to 50 mg lipid per ml. More preferred are liposomes prepared at about 3 to 30 mg lipid per ml, more preferably about 10 mg lipid per ml.

Antigen masses are generally selected based on the desired dose and the volume of the final composition that will be injected. For example, if 10 micrograms of an antigen is known to induce the desired immunogenic response and if 1 milliliter is the normal injected amount for the animal being immunized, a vaccine composition will be prepared using the guidelines set forth herein so that 1 milliliter of the final vaccine composition contains 10 micrograms of the antigen. Antigens are typically administered at concentrations of about 1 to 500 μg/ml, more commonly 10 to 50 μg/ml. However, these are only general guidelines and the specific amount of antigen must be adjusted depending on the immunogenic response as previously discussed.

In a similar manner, the amount of muramyl tripeptide (if used) is adjusted to provide a standard dose and the final vaccine composition. Such standard doses are typically in the range of from about 1 to about 2500 μg/ml, preferably about 10 to 250 μg/ml.

To ensure mixing with the emulsion, the size is generally selected to match the emulsion particle size. For example, liposomes in the range of from 200 to 450 nM in diameter have prepared for use in submicron emulsions. Unilamellar liposomes are particularly preferred.

Although at least some of the antigen is associated with the liposomes by being incorporated therein or by being associated with the liposome surface, is also possible to have compositions of the invention in which antigen is present that is not associated with the liposomes. This antigen can be present in the emulsion when the emulsion is initially prepared, or the antigen can become disassociated from the liposome composition, which will typically contain some liquid phase associated with and external to the liposomes.

The invention now being generally described, the same will be better understood by reference to the following detailed examples which are provided by way of illustration and are not intended to be limiting of the invention unless so specified.

EXAMPLES

Example 1

Physical Association of gD2 with Liposomes

Studies were carried out to demonstrate the association of antigen with liposomes, a prerequisite to delivery of antigen by liposomes to cells.

Nonfusogenic

Liposomes composed of PC/PS (7:3) were prepared both by octyl glucoside dialysis and by reverse phase evaporation (REV). gD2 at 100 μg/ml was tracked using stable iodinated gD2 as a marker. Separation of liposomes from unassociated gD2 by liquid chromatography demonstrated that 17% of gD2 associated with dialysis liposomes, and REV liposomes had 33% gD2 associated. None of the liposomes associated with gD2 was susceptible to trypsin digestion, indicating that gD2 was not present on the outer surface of the vesicles. Incubating the liposomes (2 mM lipid) overnight with 0.4 to 2 mM Triton® X-100 resulted in progressive dissociation of gD2 at higher levels of Triton®, consistent with progressive permeabilization of the liposomes. The REV liposomes were somewhat more resistant to detergent permeabilization due to the lack of residual octyl glucoside with this method.

Fusogenic

Liposomes composed of PE/GS (8:2) were prepared by octyl glucoside dialysis. Since this lipid composition was incompatible with the REV technique, we used PE/OA (8:2) for that method of preparation. The substitution of oleic acid for glycerol-succinate produces stable LUV by REV. Dialysis liposomes had 39% associated gD2 and REV liposomes had 72% association (Table 1). Of ;he associated gD2, about 50% was removed from dialysis liposomes by trypsin digestion and therefore was externally accessible. Fusogenic dialysis liposomes were more readily permeabilized by Triton® than the nonfusogenic formulation. The REV liposomes containing oleic acid lost most labeled gD2 when treated with either trypsin or Triton®. Rather than providing useful information regarding gD2 association with these vesicles, this demonstrates the intrinsic leakiness of a vesicle preparation containing 20 mole percent fatty acid. Incubation of gD2 with pre-formed PE/GS/CHOL (8:2:2) dialysis liposomes resulted in zero association of gD2 with liposomes.

TABLE 1 gD2 Association with Liposomes

| Lipid Composition | Method of Preparation | gD2 % Association | Trypsin Digestion | Triton X-100 Permeabilization |
|---|---|---|---|---|
| PC/PS (7:3) | octyl glucoside dialysis | 17 | – | ++ |
| | reverse phase | 33 | – | + |

TABLE 1-continued gD2 Association with Liposomes

| Lipid Composition | Method of Preparation | gD2 % Association | Trypsin Digestion | Triton X-100 Permeabilization |
|---|---|---|---|---|
| PE/GS (8:2) | evaporation octyl glucoside dialysis | 39 | ++ | +++ |
| PE/OA (8:2) | reverse phase evaporation | 72 | ++++ | ++++ |

− = no loss of gD2 from liposomes
+ = release of gD2 with 0.1% Triton
++ = gD2 removed from liposomes by 0.05% Triton
+++ = gD2 removed by 0.025%
++++ = total release of gD2 from liposomes by 0.025% Triton

Example 2

Physical Association of RT6 With Liposomes

In a manner similar to that described in Example 1, the association of the genetically engineered HIV reverse transcriptase molecule RT6 with liposomes was measured. RT6 associates at 29% with PC/PS (7:3) dialysis liposomes and 73% with PE/GS (8:2) dialysis liposomes. Low iodine labeling of the RT6 resulted in equivocal trypsin digestion and Triton® permeabilization effects.

Example 3

Physical Association of gp120 with Liposomes

In a similar manner, the association of HIV gp120 with PC/PS (7:3) dialysis liposomes was determined to be 8% and with PE/GS (8:2) dialysis liposomes, 11%, much lower than the association levels observed for gD2 and RT6. Gel filtration HPLC chromatograms reveal the presence of a gp120-rich peak which lies between the liposome fraction and monomeric gp120. The peak is probably mixed micelles of gp120 and octylglucoside. Trypsin digestion and Triton® permeabilization indicate the gp120 is encapsulated in both liposome preparations and is not externally accessible in either.

The association of gp120 with fusogenic liposomes was enhanced by preparing liposomes by the freeze-thaw-filter method. Association of antigen was determined by protein analysis of pelleted liposomes.

Incubation of gp120 with pre-formed freeze-thaw-filtered (FTF) liposomes of either PC/PS (7:3) or PE/GS/CHOL (8:2:2) composition resulted in zero association.

TABLE 2 gp120 Association with Liposomes

| Lipid Composition | Method of Preparation | gp120% Association | Trypsin Digestion | Triton X-100 Permeabilization |
|---|---|---|---|---|
| PC/PS (7:3) | octyl glucoside dialysis | 8 | − | ++ |
| PE/GS (8:2) | octyl glucoside dialysis | 11 | − | ++ |

TABLE 2-continued gp120 Association with Liposomes

| Lipid Composition | Method of Preparation | gp120% Association | Trypsin Digestion | Triton X-100 Permeabilization |
|---|---|---|---|---|
| PE/GS/CHOL (8:2:1) | freeze-thaw-filter | 56 | ND | ND |

− = no loss of gp120 from liposomes
++ = gp120 removed from liposomes by 0.1% Triton
ND = not determined

Example 4

Association of Malaria Sera 1 with Liposomes

The association of malaria sera 1 protein with PC/PS (7:3) liposomes was 67% with dialysis liposomes and 95% with FTF liposomes. Sera 1 added to preformed liposomes associated 75% with FTF vesicles. Sera 1 association with PE/GS/CHOL (8:2:2) liposomes was 65% with dialysis liposomes and 87% with FTF liposomes. Sera 1 associated at 91% with pre-formed dialysis liposomes. Unbound protein was separated from liposomes by centrifugation. Antigen association was determined by protein assay of liposome pellets.

Example 5

Physical Association of Influenza HA Taiwan with Liposome

HA Taiwan associated at 69% with DPPC/DMPG (8:2) dialysis liposomes. HA Taiwan associated at 78% with PE/GS/CHOL (8:2:2) dialysis liposomes and at 80% with pre-formed vesicles. Association was measured as described for Sera 1.

Example 6

Physical Association of HSV gB2 Peptide with Liposomes

HSV gB2 peptide associated at 40% with PC/PS (7:3) FTF liposomes, determined as described for Sera 1.

Example 7

Physical Association of gB2 with Liposomes

HSB gB2 associated at 24% with PE/GS/CHOL (8:2:2) liposomes prepared by dialysis. The association of gB2 is 84% when the liposomes are prepared by FTF. Protein association was determined by removing unbound gB2 by centrifugation and measuring gB2 associated with the liposome pellet by capture ELISA.

Example 8

In Vitro Studies on Antigen Uptake and Cellular Localization

Studies were undertaken to determine the intracellular fate of antigen using the compositions of the invention.

Initial experiments to demonstrate uptake of FITC-dextran loaded liposomes by murine and human macrophages have been consistently successful. Liposomes prepared by reverse phase evaporation and by high pressure extrusion are taken up equally well. Nonfusogenic lipid compositions used were PC/PS at a mole ratio of 7:3 and PC/phosphatidylglycerol at 9:1. Fusogenic lipid compositions were either PE/CHOL/OA at 4:4:2 or PE/OA at 8:2. To form fusogenic liposomes, the aqueous phase is initially at pH 10. Upon exchange of the external volume by gel filtration at pH 7.4, the liposomes are stable for at least two days, based on phase contrast and epifluorescence microscopy.

An eighteen hour pulse of nonfusogenic liposomes with macrophages produces bright punctate fluorescence inside the cells. Pulse chase experiments demonstrate that liposomes are first present at the periphery of the cytosol, then move to the perinuclear region. This is consistent with endosomal uptake followed by intracellular transport to lysosomes. Incorporation of MTP-PE into the bilayer at the lipid:MTP-PE mole ratio of 250:1 had no effect on uptake kinetics.

Similar experiments done with fusogenic liposomes resulted in a combination of bright punctate fluorescence and dim diffuse fluorescence. Pulse chase experiments did not entirely eliminate the punctate fluorescence, suggesting that endosomal fusion is less than 100% efficient. Furthermore, liposome titration experiments show that fusion can be overwhelmed: greater than 100 µg phospholipid/$10^4$cells/cm$^2$ produced heavily loaded punctate fluorescence with some diffuse fluorescence, whereas less than 10 µg phospholipid/$10^4$ cells/cm$^2$ produced predominantly diffuse fluorescence. Incorporation of MTP-PE at phospholipids MTP-PE mole ratios of 1000:1, 500:1, and 250:1 resulted in extremely faint levels of both diffuse and punctate fluorescence, with the effect most marked below 1000:1. Free FITC-dextran was not endocytosed under these conditions, strongly suggesting that the shutdown of endocytosis is not a surface effect, but rather a result of MTP-PE entering the cytosol. Preliminary experiments with FITC-gD2 loaded liposomes indicate that gD2 is readily delivered into macrophages by this method.

Example 9

Macrophage Uptake we compared the uptake of FITC-dextran-loaded liposomes by U937 cells, a human monocyte-like cell line from American Type Culture Collection, to our previous uptake experiments with primary macrophage cultures. Undifferentiated U937 cells did not phagocytose either liposomes or free FITC-dextran. If the cells were differentiated with phorbol-myristic-acetate and incubated 18 hours with nonfusogenic PC/PG (8:2) liposomes, they acquired punctate fluorescence indicating uptake of the dextran into endosomes or lysosomes. Incubation with fusogenic PE/GS (8:2) liposomes produced uniform diffuse fluorescence indicating delivery of the dextran to the cell cytoplasm. Incorporation of MTP-PE in the liposomes did not affect phagocytosis. While these results are similar to those observed in true macrophages, a major difference between the two cell types is in rate of uptake: differentiated U937 cells require about ten times as much lipid as macrophages to acquire visible amounts of fluorescence. For macrophages, phagocytosis itself is an activation signal. U937 cells may not be activated by phagocytosis.

U937 cells matured with 25 ng/ml PMA for 5 days were incubated overnight with soluble gD2, nonfusogenic PC liposomes with gD2, and fusogenic PE liposomes with gD2. The presence of intracellular gD2 was assessed by immunofluorescence of FITC-goat-α mouse Ab bound to mouse-α a gD Mab.

We found that soluble gD2 resulted in lower levels of fluorescence than either liposome preparation, and that PE liposomes produced higher fluorescence levels than PC liposomes. Overall, the same pattern of uptake was observed whether the cells were incubated in the presence or absence of 10% serum, with fluorescence being somewhat higher in the presence of serum. Cells incubated with soluble gD2 had low levels of diffuse fluorescence. Cells incubated with either liposome preparation had predominantly diffuse fluorescence with occasional punctate fluorescence. These results are in contrast to our earlier experiment with FITC-dextran-loaded liposomes in which diffuse fluorescence was associated with fusogenic liposomes and punctate fluorescence was observed with nonfusogenic liposomes. Since gD2 is a pH-insensitive fusogenic protein, it may be inducing fusion of both types of liposomes with the cells, which would produce diffuse fluorescence.

The experiments above suggested that gD2 may alter the intracellular localization of liposome contents. To test this, U937 cells were incubated overnight with liposomes prepared with either gD2 and FITC-dextran or gD2 and RT6. Epifluorescence microscopy showed that PC/PS liposomes produced a punctate pattern of fluorescence for both FITC-dextran and RT6. In the case of PE/GS liposomes, diffuse fluorescence was observed for both FITC-dextran and RT6. Under these conditions, gD2 is not able to alter the localization of liposome contents.

Example 10

Immunogenicity of Liposome/Emulsion Combinations with gD2 in goats

These data show that for a given emulsion, higher antibody titers are obtained if the antigen is combined with liposomes prior to mixing with emulsion. The antibody titers elicited by either fusogenic or nonfusogenic liposomes are approximately equivalent when mixed with emulsions.

In an this experiment, a composition consisting of an oil-in-water emulsion containing MTP-PE, designated MF79/1501 (10% squalene (v/v); 1% Tween ® 80 (v/v); 5% Tetronic® 1501 (a polyoxyetheylene-polyoxypropylene block polymer) (v/v); 400 μg/ml MTP-PE), combined with the gD2 antigen was tested for immunogenicity. This composition was then compared to the combination of MF79/1501 plus fusogenic liposomes. This liposome-gD2 mixture was used to immunize animals three times at three-week intervals. As seen in Table 3, this combined emulsion-liposome immunization gave high antibody responses. After two immunizations the liposome plus emulsion group showed a mean titer of 7258, approximately three-fold higher than the M79/1501 emulsion alone. This response was very consistent within the group with a standard error of only 10%. After the third immunization, all animals in the group showed moderate increases in titer except one. Thus combining liposomes with emulsions offered significant increases in immune response.

TABLE 3 gD2 Adjuvant Study in Goats

| Animal Number | Adjuvant | Pre-bleed | Mean[a] ELISA Titer for Bleeds 1/2[b] | 2/2 | 3/2 |
|---|---|---|---|---|---|
| 5026 | 2x MF59 | (<5) | 37 | 448 | 800 |
| 5035 | (internal | (<5) | 385 | 802 | 741 |
| 6156 | control)* | (<5) | 40 | 191 | 450 |
| 6511 | | (<5) | <5 | 887 | 617 |
| 6629 | | (<5) | 144 | 941 | 576 |

TABLE 3-continued gD2 Adjuvant Study in Goats

| Animal Number | Adjuvant | Pre-bleed | Mean[a] ELISA Titer for Bleeds | | |
|---|---|---|---|---|---|
| | | | 1/2[b] | 2/2 | 3/2 |
| | | (<5) | 53 + 39 | 564 + 170 | 624 + 63 |
| 5031 | MF79/1501 | (<5) | 3,277 | 4,456 | 8,766 |
| 6153 | | (<5) | 125 | 870 | 5,189 |
| 6165 | | (<5) | 96 | 1,173 | 1,204 |
| 6517 | | (<5) | 784 | 3,830 | 10,706 |
| 6626 | | (<5) | 40 | 4,009 | 4,113 |
| | | (<5) | 262 + 209 | 2,338 + 810 | 4,747 + 1,823 |
| 5033 | MF79/1501 | (<5) | 598 | 7,381 | 10,633 |
| 6155 | + | (<5) | 869 | 5,878 | 8,683 |
| 6510 | Liposomes | (<5) | 846 | 10,517 | 14,995 |
| 6519 | | (<5) | 279 | 6,354 | 13,079 |
| 6628 | | (<5) | 235 | 6,945 | 1,845 |
| | | (<5) | 492 + 136 | 7,258 + 729 | 8,039 + 3,041 |

[a]Geometric mean + standard error.
[b]Bleed identification: Number of immunizations/weeks post immunization.
*2x MF59 = 10% squalene (v/v); 0.4% Tween 80 (v/v); 1.6% Span 85 (v/v); 400 µg/ml MTP-PE

Example 11

Effects of Emulsion/Liposome Combinations With gD2 in Goats on Antibody Titers

In this experiment, goats were immunized with gD2 (25 µg) combined with several emulsions, liposome/emulsion combinations, and liposomes alone. Liposome/emulsion combinations tested were PE/GS liposomes plus 2×MF59, PE/GS liposomes plus MF79/5% Tetronic® 1501, and PC/PS liposomes plus MF79/5% Tetronic®1501. Controls in this experiment included alum, and 2×MF59. All MTP-PE doses were 100 µg. With liposome emulsion combinations approximately 50% of the antigen was entrapped in liposomes and 50% was free in solution. All MTP-PE was in the emulsion phase in liposome/emulsion combinations. In the liposome alone group, MTP-PE was added exogenously to the liposomes. Animals were immunized three times at three-week intervals and anti-gD2 antibody titers were determined 14 days after each immunization (results are shown in Table 4).

Combinations of MF79/5% 1501 and PE/GS liposomes (fusogenic LUV) gave much higher anti-gD2 titers than MF59 emulsion alone. The current results demonstrate that combinations of PE/GS liposomes with 2×MF59 do not perform as well as PE/GS liposomes combined with MF79/5% 1501. PE/GS liposomes do improve the performance of 2×MF59. PE/GS liposomes alone give very poor anti-gD2 antibody response. Combination of PC/PS liposomes with M179/5% 1501 perform equivalently to PE/GS liposomes combined with MF79/5% 1501 (mean titer after three immunizations of 6946 vs. 4653).

TABLE 4 gD2 Adjuvant Study in Goats

| Adjuvant | Prebleed | Mean ELISA Titer for Bleeds | | |
|---|---|---|---|---|
| | | 1/2 | 2/2 | 3/2 |
| 2x MF59 | <5 | <5 | 144 + 85 | 837 + 169 |
| 2x MF59 + Liposomes (PE/GS) | <5 | <5 | 344 + 187 | 1440 + 842 |
| MF79/1501 + Liposomes (PE/GS) | <5 | <5 | 1000 + 328 | 4653 + 616 |
| Alum | <5 | <5 | 39 + 24 | <5 |
| MF79/1501 + Liposomes (PC/PS) | <5 | 58 + 61 | 1980 + 416 | 6946 + 1503 |
| Liposomes (PE/GS) + MTP exogenous | <5 | <5 | 6 + 1 | 6 + 1 |

Example 12

Effects of gD2 Association with Liposomes on the Immunogenicity of Liposome/Emulsion Combinations in Goats In this experiment goats were immunized 3 times with 25 µg gD2 and 100 µg MTP-PE at four-week intervals with one of the following adjuvants:

1. MF79/121 (10% squalene, 1% Tween 80, 5% Pluronic L121, 400 µg/ml MTP-PE); 2. MF79/121 combined with LPC (PC/PS (7:3) dialysis liposomes), such that 50% of the gD2 was associated with the liposomes and 50% of the gD2 was free in the aqueous phase of the formulation; 3. MF79/L121 combined with the LPC such that 100% of the gD2 was associated with the liposomes. As shown in FIG. 1, an increase in antibody titers is correlated with increased antigen association with liposomes. Geometric mean antibody titers for groups of 5 animals are given in Table 5. Enhanced Ab titers persisted for at least six weeks after a fourth immunization.

TABLE 5 gD2 Adjuvant Study in Goats

| Number Animals | Adjuvant | Prebleed | Bleed 2/13[a] | Bleed 3/14[a] | Bleed 3/90 | Bleed 4/7 | Bleed 4/21 | Bleed 4/42 |
|---|---|---|---|---|---|---|---|---|
| 5 | MF79/L121 | <5 | 888 ± 179 | 2,582 ± 948 | 60 ± 28 | 3,782 ± 917 | 2,267 ± 692 | 492 ± 196 |
| 5 | MF79/L121 + | <5 | 1,418 ± 391 | 6,884 ± 1,274 | 115 ± 51 | 6,229 ± 1,544 | 7,987 ± 1,250 | 1,241 ± 345 |
| 5 | MF79/L121 + Liposomes B (100*) | <5 | 784 ± 628 | 13,449 ± 1,908 | — | — | — | — |
| 5 | MF79/L121 + Liposomes B (50/50* + MTP) | <5 | 945 ± 609 | 4,563 ± 2,563 | — | — | — | — |

TABLE 5-continued

| | | | gD2 Adjuvant Study in Goats | | | | | |
|---|---|---|---|---|---|---|---|---|
| Number Animals | Adjuvant | Prebleed | Bleed 2/13[a] | Bleed 3/14[a] | Bleed 3/90 | Bleed 4/7 | Bleed 4/21 | Bleed 4/42 |
| 5 | Liposomes C (50/50* + MTP) | 6 ± 1 | <5 | 9 ± 2 | 19 ± 5 | <5 | 6 ± 1 | 12 ± 5 |
| 5 | MF79/1501 + Liposomes A (50/50*) | <5 | 2,068 ± 268 | 7,864 ± 1,253 | — | — | — | — |

[a]geometric mean ± standard error.
[b]immunization No/days past immunization; MTP-PE at 100 µg/dose.
[c*]gD2 antigen at 25 µg dose. incorporation ratio of gD2 and/or MTP in liposomes.

Example 13

Effects of gB2 Association with Liposomes on the Immunogenicity of Liposome/Emulsion Combinations in Goats In this experiment, goats were immunized three times at four week intervals with 5, 25, or 100 µg of gB2 and 100 µg of MTP-PE with one of the following adjuvants: 1, MF79/121, as defined in Example 2, MF79/121 combined with LPE (PE/GS/CHOL (8:2:2) FTF liposomes) such that 50% of the gB2 was associated with the liposomes and 50% was free in solution; 3, MF79/L121 combined with LPE such that 100% of the gB2 was associated with the liposomes.

Figure 2:
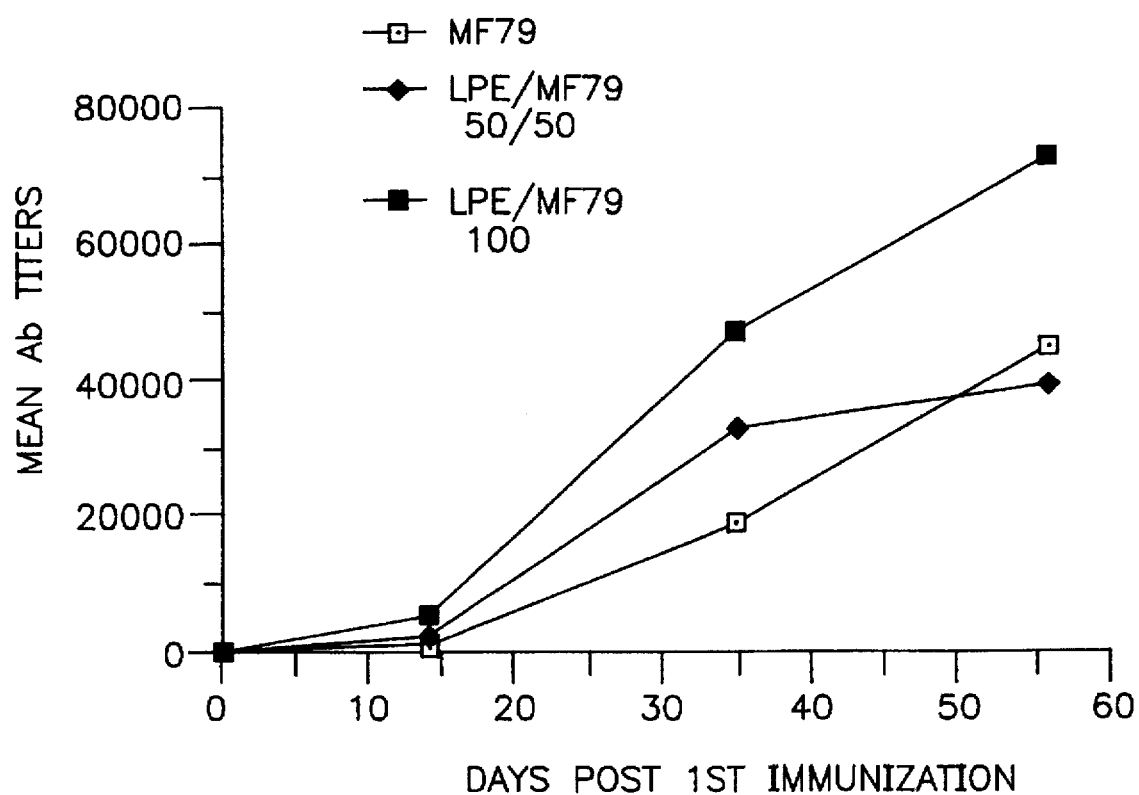
FIG. 2 is a graph showing mean antibody titers at different times after immunization with the antigen gB2 in goats using different env2-3 adjuvant formulations.

The effects of antigen association with liposomes for the 25 µg gB2 dose groups are shown in FIG. 2. Again, immunogenicity increases with increases in antigen association with liposomes. The geometric mean antibody titers: standard error for each group of animals are given in Table 6.

Example 14

Immunogenicity of Liposome/Emulsion Combination Using gp120 in Rhesus Monkeys

Figure 3:
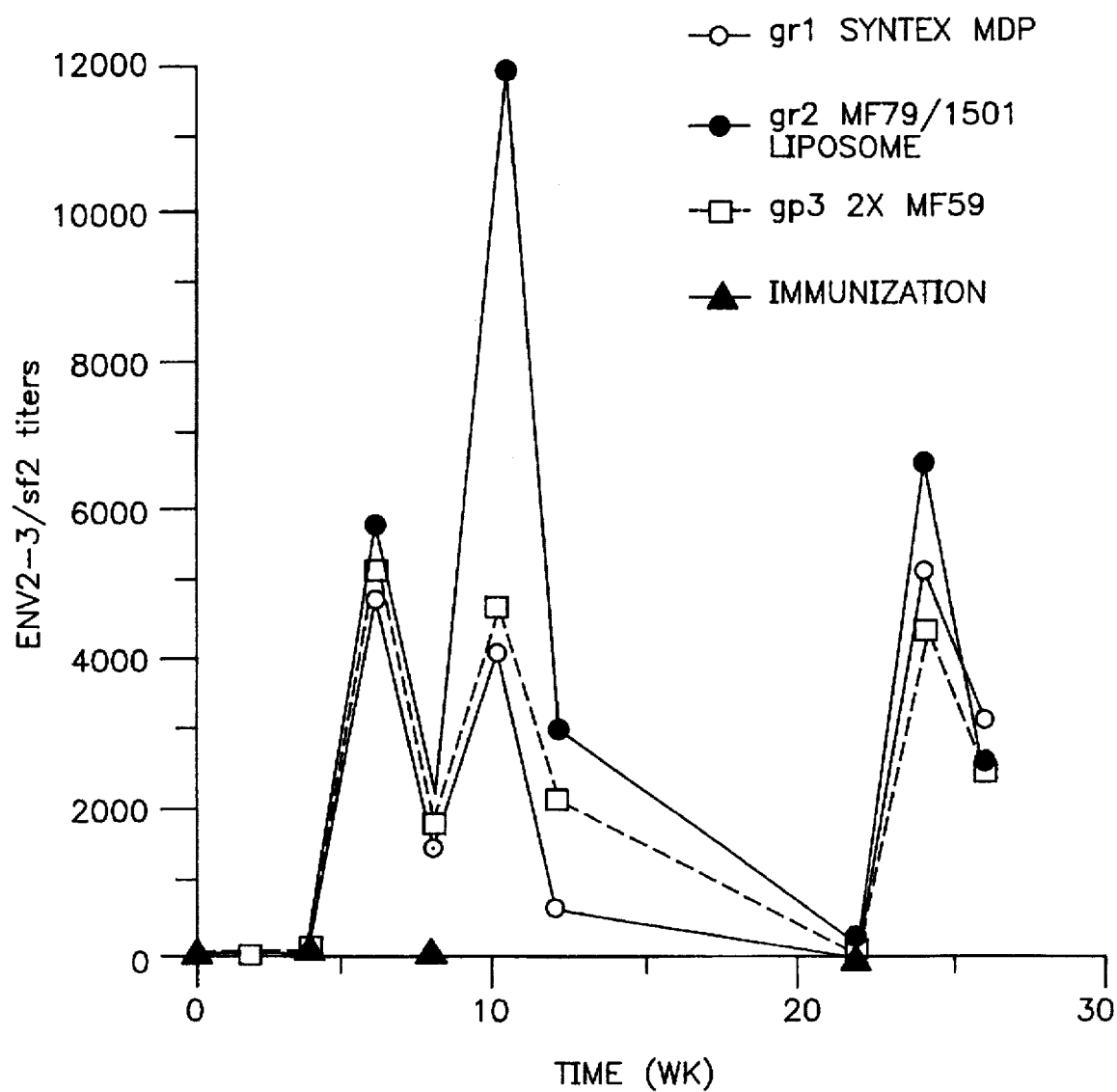
FIG. 3 is a graph showing mean antibody titers at different times after immunization with the antigen env203/sf2 in rhesus monkeys using different adjuvant formulations.

In this experiment, groups of 3 rhesus monkeys were immunized 3 times at 4-week intervals and one time 14 weeks after the third immunization. Animals were bled ever; 2 weeks throughout the experiment. One group received MF79/1501 (10% squalene, 1% Tween 80, 5% Tetronic 1501, 400 µg/ml MTP-PE) combined with LPE FTF liposomes containing gp120/SF2. The other two groups received either 2XMF39 (10% squalene, 1% Tween 80, 1% Span 83, 400 µg/ml MTP-PE) or SAF emulsion (10% squalene, 5% Pluronic L121, 0.4% Tween 80, 500 µg/ml MDP). FIG. 3 illustrates that MF79/1501 and liposomes produced consistently higher titers than the other 2 emulsion formulations. Table 7 lists both individual animal titers and mean titers for each group throughout the experiment.

TABLE 6

| Group | Ag Association[b] | Number of Animals | Adjuvant[a] | Prebleed Mean | Bleed 1/14 Mean | Bleed 2/14 Mean | Bleed 3/14 Mean |
|---|---|---|---|---|---|---|---|
| 1 | — | 5 | MF79/L121-MTP (5 µg gB2) | <5 | 1,678 ± 473 | 29,656 ± 3,218 | 33,325 ± 3,100 |
| 2 | 0 | 5 | MF79/L121-MTP (25 µg gB2) | <5 | 434 ± 129 | 18,609 ± 3,962 | 44,846 ± 5,203 |
| 3 | — | 5 | MF79/L121-MTP (100 µg gB2) | <5 | 412 ± 131 | 35,161 ± 4,959 | 42,228 ± 7,585 |
| 4 | — | 5 | MF79/L121-MTP + Liposomes (A) (5 µg gB2) | <5 | 1,666 ± 413 | 17,565 ± 3,610 | 36,700 ± 6,230 |
| 5 | 100 | 5 | MF79/L121-MTP + Liposomes (A) (25 µg gB2) | <5 | 5,096 ± 1,716 | 47,285 ± 10,173 | 73,109 ± 13,199 |
| 6 | — | 5 | MF79/L121-MTP + Liposomes (A) (100 µg gB2) | <5 | 1,289 ± 422 | 38,544 ± 6,263 | 59,493 ± 13,706 |
| 7 | 50/50 | 5 | MF79/L121-MTP + Liposomes (B) (25 µg gB2) | <5 | 1,733 ± 844 | 32,835 ± 12,628 | 39,746 ± 14,871 |
| 8 | — | 5 | Liposomes (C)MTP* MF79/L121-MTP (25 µg gB2) | <5 | 152 ± 85 | 12,022 ± 3,825 | 25,163 ± 3,044 |

*1st boost with Liposomes
2nd and 3rd with MF79/L121
[a]All MTP-PE doses are at 100 µg/dose.
[b]Ag association is shown only for the composition that appear in FIG. 2:
0 = gB2 free in aqueous phase;
100 = gB2 all associated with liposomes; and
50/50 = gB2 associated 50% with liposomes and 50% free in aqueous phase.

TABLE 7

Summary of Individual Antibody Titers, Mean Antibody Titers Per Group ± Standard Error

| Immunization | Time(wk) | bleed# | 8428 | 8429 | 8430 | gr1 $\bar{X}$ | gr1.0 ± SE | 8431 |
|---|---|---|---|---|---|---|---|---|
| 1 | 1 | 0 | .0 | 1 | 1 | 1 | 1 | 0 | 1 |
| 2 |   | 2 | .01 | 50 | 50 | 1 | 14 | 17 | 1 |
| 3 | 2 | 4 | .02 | 70 | 50 | 50 | 56 | 6 | 50 |
| 4 |   | 6 | .03 | 4300 | 5100 | 5600 | 4971 | 384 | 4900 |
| 5 | 3 | 8 | .04 | 1500 | 1400 | 1800 | 1558 | 117 | 1600 |
| 6 |   | 10 | .05 | 5218 | 4841 | 2925 | 4196 | 762 | 6746 |
| 7 |   | 12 | .06 | 1442 | 1 | 649 | 714 | 365 | 1915 |
| 8 | 4 | 22 | .07 | 117 | 75 | 109 | 100 | 14 | 142 |
| 9 |   | 24 | .08 | 5574 | 6808 | 4093 | 5375 | 796 | 5397 |
| 10 |   | 26 | .09 | 3335 | 3405 | 3368 | 3369 | 20 | 1768 |

|    | 8432 | 8433 | gr2 $\bar{X}$ | gp2.0 ± SE | 8434 | 8435 | 8436 | gp3 $\bar{X}$ | gp3.0 ± SE |
|---|---|---|---|---|---|---|---|---|---|
| 1 | 1 | 1 | 1 | 0 | 1 | 1 | 1 | 1 | 0 |
| 2 | 89 | 1 | 60 | 11 | 50 | 50 | 82 | 59 | 9 |
| 3 | 70 | 50 | 56 | 6 | 50 | 50 | 105 | 64 | 15 |
| 4 | 10200 | 3900 | 5798 | 1681 | 6200 | 3700 | 6900 | 5409 | 1041 |
| 5 | 4300 | 1200 | 2021 | 781 | 2700 | 1100 | 2300 | 1897 | 525 |
| 6 | 14162 | 14713 | 11874 | 2843 | 5471 | 8869 | 14790 | 4712 | 1956 |
| 7 | 3880 | 4263 | 3164 | 800 | 1569 | 2156 | 3014 | 2168 | 408 |
| 8 | 338 | 411 | 270 | 88 | 165 | 119 | 221 | 263 | 29 |
| 9 | 8808 | 6646 | 6811 | 967 | 4372 | 3386 | 6459 | 4573 | 859 |
| 10 | 4683 | 2503 | 2747 | 783 | 2471 | 1475 | 4886 | 2611 | 906 |

Example 15

Figure 4:
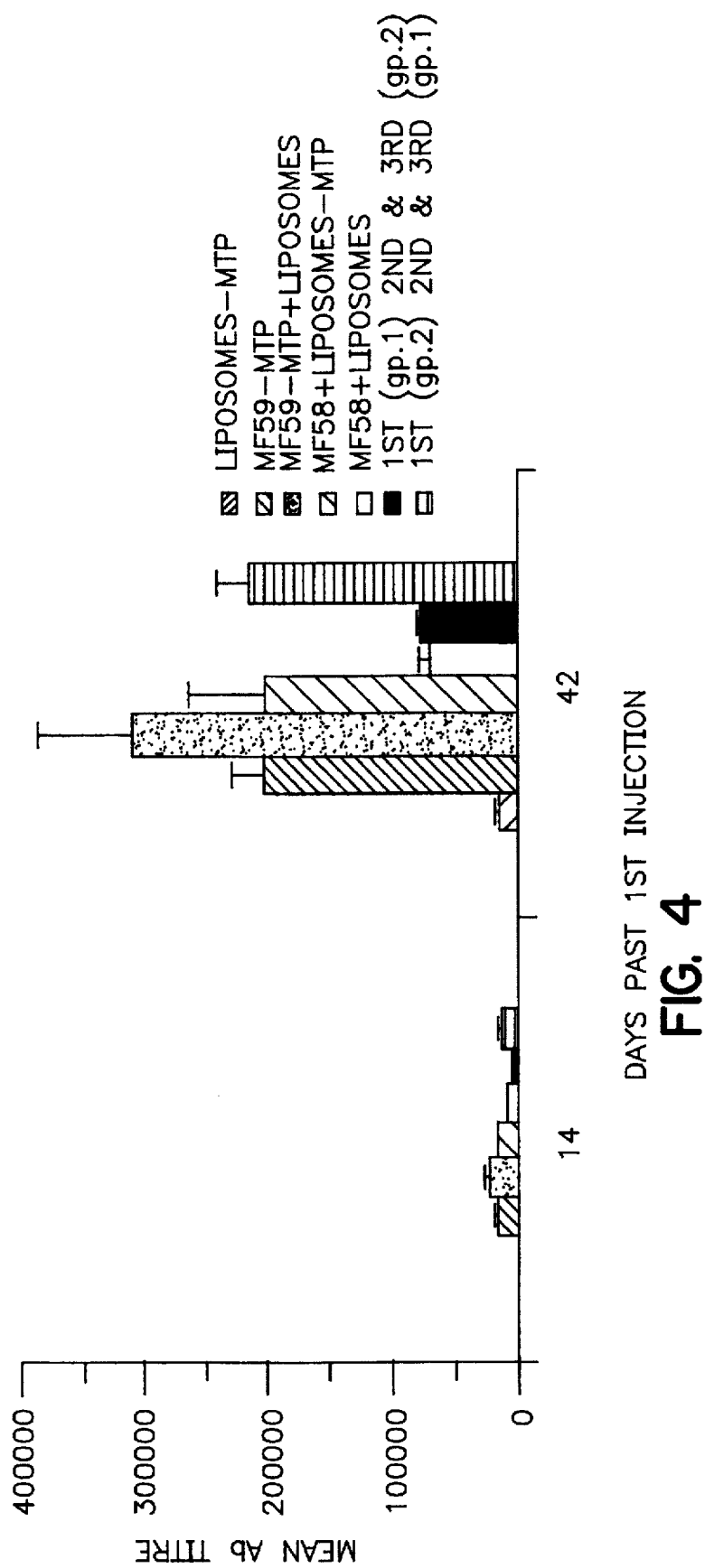
FIG. 4 is a graph showing mean antibody titers at different times after immunization with the antigen gD2 in rabbits using different adjuvant formulations.

Effects of MTP-PE Association with Liposomes or Emulsion on the Immunogenicity of gD2 Combination Formulations in Rabbits Rabbits were immunized three times at four week intervals with 10 μg gD2 and 100 μg MTP-PE. The results of this experiment, up to two weeks after the second immunization are included here in FIG. 4 and Table 8. Comparison of groups 2 and 3, Table 8, shows that again immunogenicity was enhanced by combining emulsion MF59 (5% squalene, 0.5% Tween 80, 0.5% Span 85, 400 μg/ml MTP-PE) with gD2 prepared with LPE. Including MTP-PE in the emulsion, group 3, or the liposomes, group 4, did not produce significant changes in immunogenicity. Group 6 was immunized once with LPE and then boosted 2 times with MF59, group 7, the order was reversed, the animals first receiving an injection of MF59 followed by 2 immunizations with LPE. Clearly, priming with emulsion and boosting with liposomes is more immunogenic than the converse. The earlier cited Goat gB2 experiment (example 13, Table 6, group 8) confirms poor response when the animals were primed with liposomes and boosted with emulsion.

TABLE 8

Rabbit/gD2 - MTP-PE Association

| Group | Bleed 1/2 | Bleed 2/2 |
|---|---|---|
| 1 LPE with MTP-PE | 468 ± 191 | 12254 ± 3517 |
| 2 MF59 | 14418 ± 2698 | 200764 ± 32488 |
| 3 MF59/LPE | 20859 ± 4508 | 307828 ± 75470 |
| 4 MF58/LPE with MTP-PE | 15241 ± 1203 | 202640 ± 58941 |
| 5 MF58/LPE | 6330 ± 903 | 68069 ± 8127 |
| 6 1X LPE with MTP-PE 2X MF59 | 1140 ± 160 | 72001 ± 3741 |

TABLE 8-continued

Rabbit/gD2 - MTP-PE Association

| Group | Bleed 1/2 | Bleed 2/2 |
|---|---|---|
| 7 1X MF59 2X LPE with MTP-PE | 11272 ± 3117 | 211980 ± 25964 |

- gD2 at 10 μg/dose
- MTP-PE at 100 μg/dose; group 5 received no MTP-PE
- 5 animals per group

Example 16

Effects of Emulsion/Liposome Combination on the Immunogenicity of Malaria Sere 1 in Aotus Monkeys Aotus monkeys were immunized three times at four week intervals with 100μg of Sere 1. Eighty-four days after the first immunization, the animals were bled and challenged with the Honduras strain of Plasmodium falciparum. The monkeys were subsequently monitored for both disease and perasitemia.

Figure 5:
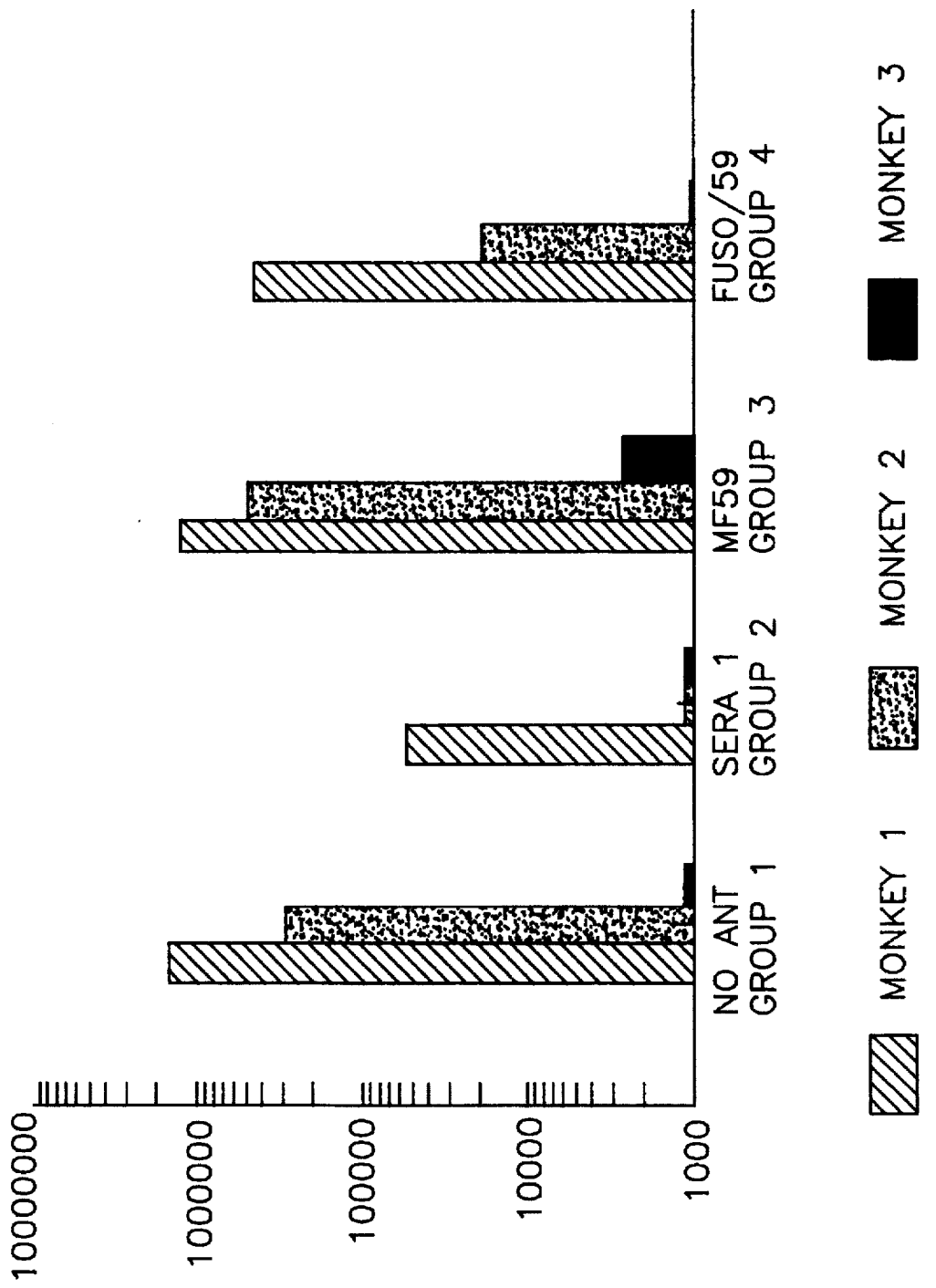
FIG. 5 is a graph showing cumulative parasitemia in several groups of monkeys immunized with a malarial antigen and different adjuvants and then challenged with heterologous malaria.

Antibody titers on day 84 and later protection from disease are shown in Table 9. Group 1 received only Freund's adjuvant and no antigen. Group 2 received Freund's adjuvant and Sere 1. Groups 3 and 4 received Sera 1 and either MF59 or MF59 with LPE, respectively. The combination formulation produced a 5-fold increase in Ab titers compared to emulsion alone. In both groups, one out of three animals was protected from disease. FIG. 5 shows the corresponding cumulative parasitemia scores. The parasitemia scores for the combination group 4 were nearly 10-fold lower than for group 3, which received

TABLE 9

Panama SERA 1 Aotus Monkey Trial #2
ELISA Titers of Aotus SERA 1 Antisera

|  | Prebleed | Final Bleed Day of Challenge | Mean Titers | Protection |
|---|---|---|---|---|
| Group 1 |  | 92 |  |  |
| Control CFA/IFA | <10 | 88 | 87 | 0/3 |
|  | <10 | 81 |  |  |
| Group 2 | <10 | 465,021 |  |  |
| Control CFA/IFA | <10 | 909,318 | 719,333 | 2/3 |
| SERA 1 | 19 | 783,661 |  |  |
| Group 3 | 191 | 20,258 |  |  |
| SERA 1 MF59.2 | 336 | 13,718 | 31,200 | 1/3 |
|  | <10 | 59,625 |  |  |
| Group 4 | 13 | 141,295 |  |  |
| SERA 1 | 24 | 254,074 | 169266 | 1/3 |
| Liposome/MF59.2 | <10 | 112,430 |  |  |

Group No.:
(1) Control FCA/FIA
(2) SERA 1 FCA/FIA
(3) SERA 1 MF59.2
(4) SERA 1 Fusogenic Liposomes/MF59.2

Example 17

Immunogenicity of Emulsion/Liposome Combinations in a Mouse Influenza Challenge Model This experiment was designed to test the efficacy of adjuvant formulations in a heterologous viral challenge.

survival. HA vaccine without adjuvant had 40% survival compared to a 30% survival rate for the unimmunized group.

TABLE 10

Mouse/Influenza

| Group | HA A/Shanghai |
|---|---|
| 1 HA only | 259 ± 60 |
| 2 MF59 | 7822 ± 514 |
| 3 1X MF77 | 28749 ± 3778 |
| 1X MF59 |  |
| 4 1X MF77 w/o MTP-PE + LPE + MTP-PE | 44257 ± 5234 |
| 1X MF58 + LPE + MTP-PE |  |
| 5 LPE + MTP-PE | 1579 ± 184 |
| 6 No immunization | <5 | n = 10

MTP-PE dose = 40 µg

HA = 9 µg of Parke-Davis influenza vaccine containing 30 µg/ml each of: A/Taiwan/1/86, A/Shanghai/11/87, and B/Yamaguta/16/88

TABLE 11

Taiwan Immunization
Hong Kong Challenge
Daily Record of Number of Surviving Animals Per Group

| Group | Day 0 | 1 | 2 | 3 | 4 | 5 | 6 | 7 | 8 | 9 | 10 | 11 | 12 | 13 |
|---|---|---|---|---|---|---|---|---|---|---|---|---|---|---|
| 1 HA alone | 10 | 10 | 10 | 10 | 10 | 9 | 7 | 5 | 5 | 4 | 4 | 4 | 4 | 4 |
| 2 MF59.1 | 10 | 10 | 10 | 10 | 10 | 10 | 9 | 7 | 6 | 4 | 4 | 4 | 4 | 4 |
| 3 MF77.1/MF59 | 10 | 10 | 10 | 10 | 10 | 10 | 10 | 10 | 9 | 9 | 9 | 9 | 9 | 9 |
| 4 MF77.1 + Lips MF59 + Lips | 10 | 10 | 10 | 10 | 10 | 10 | 10 | 10 | 10 | 10 | 10 | 10 | 10 | 10 |
| 5 Liposomes | 10 | 10 | 10 | 10 | 10 | 10 | 10 | 8 | 7 | 7 | 7 | 6 | 6 | 6 |
| 6 0 | 10 | 10 | 10 | 10 | 10 | 10 | 8 | 3 | 3 | 3 | 3 | 3 | 3 | 3 |

Figure 6A:
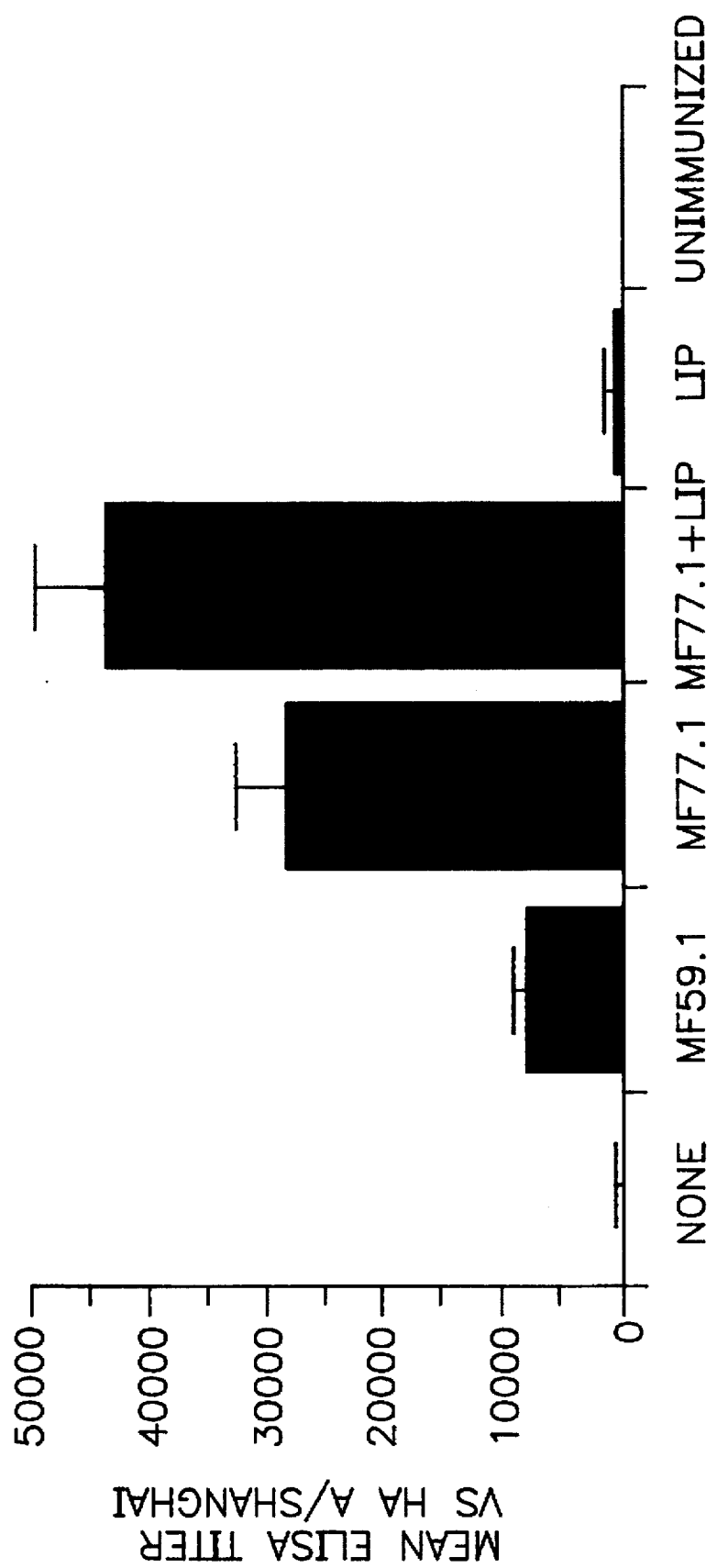
FIG. 6A and 6B are a set of two graphs showing ELISA titer (6A) and survival (6B) for mice immunized with an influenza vaccine and different adjuvants and then challenged with influenza.
Figure 6B:
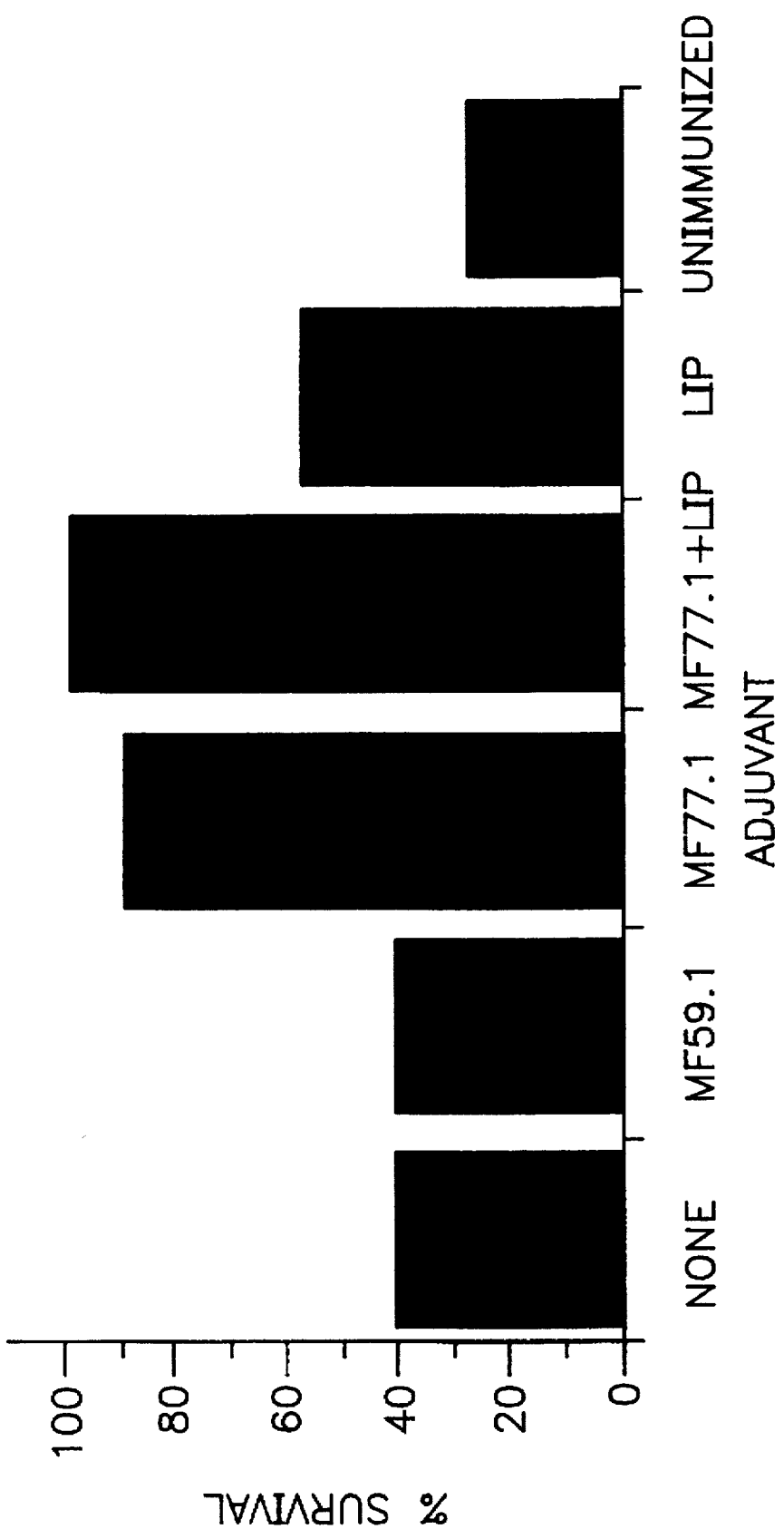

Mice were immunized two times at a four week interval with 9 µg of HA antigen and 40 µg MTP-PE. The animal groups are defined in Table 10. Group 1 received HA without adjuvant. Group 2 received MF59. Group 3 received one immunization with MF77 (10% squalene, 5% Pluronic L121, 1% Tween 80, 400 µg/ml MTP-PE), followed by a second immunization with MF59. Group 4 received one immunization with a combination formulation containing MF77 lacking MTP-PE and LPE with MTP-PE, followed by a second immunization with MF58 and LPE with MTP-PE. Group 5 received LPE with MTP-PE. Group 6 was not immunized. The antibody titers in Table 10 are for day 55, just prior to viral challenge. The highest titers were obtained in Group 4 with the combination formulation. FIG. 6 illustrates the relative Ab titers for all the groups. On day 56, the mice were challenged intranasally with influenza A/Hong Kongp/13/68 (H1N1). The animals were monitored daily for disease, and the daily survival record is shown in Table 1:1. The percentage survival 14 days after challenge is shown in the lower panel of FIG. 6. The combination formulation had 100% survival, the next best group was MF77 with 90%

Example 18

Stability of Liposome/Emulsion Combinations

To assess the physical stability of a mixture of emulsion particles and liposomes, we prepared PE/GS (8:2) /MTP-PE (PL/MTP-PE, 20:1) dialysis liposomes containing FITC-dextran. External FITC-dextran was removed by gel filtration and the liposomes were mixed with MF79/1501 (10% squalene/1% Tween 80/5% Tetronic 1501/400 µg/ml MTP-PE). Observations by light microscopy indicated no aggregation or coalescence of either emulsion particles or liposomes. Structural integrity of the liposomes was further confirmed by observation of fluorescent spheres against a dark background. No change in appearance has occurred after 3 months storage at 4° C.

Example 19

Storage of Liposomes and Emulsions

In order for the liposomes containing the antigens (encapsulated or incorporated by surface adsorption or integration into bilayer) and emulsions as a combination to be viable pharmaceutical entities, stable storage conditions and storage forms are explored. Three different dosage forms are designed to enhance the stability of the adjuvants and antigens; 1) Liquid liposome suspension-emulsion combinations in two vials or single vial storable at 2°–8° C. 2) Frozen liposomes—emulsion combination in two separate vials or single vial storable at 5°–10° C. 3) Lyophilized liposomes—emulsion in two separate vials or single vial storable at 2°–8° C. or ambient temperature.

A slightly acidic pH ($\geq 5.0=\leq 7.0$ preferably 6.5) is chosen for these formulations to improve the stability of the lipid components and the protein antigens. Cryoprotectants (for lyophilizations and freezing) are selected from the following list of sugars or polyhydroxylic compounds and amino acids: dextrose, mannitol, sorbitol, lactose, sucrose, trehalose, glycerol, dextran, maltose, maltodextrins, glycine, alanine, proline, arginine, and lysine. In some formulations, a combination of sugars and amino acids e.g. sucrose-mannitol (sucrose 5–8% w/v, mannitol 2.5–1% w/v); sucrose-glycine (sucrose 8% w/v, glycine 60 mm) are used. These excipients also served as tonicifiers, i.e., provided physiologic osmolality. Buffers are selected from a group consisting of phosphate (5–50 mM); citrate; phosphate buffered saline (PBS); acetate; maleate; ascorbate; tromethamine; and similar buffers.

In the case of liposomes, the cryoprotectants and buffers are included in a) both the aqueous interior and exterior or b) added only externally. In the latter instance, any buffer or salt (e.g. NaCl) provided osmotic balance for the interior, and the external salt is removed by repeated centrifugation and washing. The liposomes are then suspended in the excipient mixture of this invention. Emulsions are typically prepared in water and suspended in the medium discussed above. In addition to the sugar/amino acid/buffer combinations, viscosity enhancers are also added to some formulations generally believed that these polymeric substances coat the particles and prevent contact which otherwise would result in aggregation, fusion or coalescence. Polymers used include polyethylene glycol 300, 400, 1450, and 3150; polyvinyl pyrrolidone; dextran sulfate; carboxymethyl cellulose; hydroxyethylcellulose and alginic acid. Polyethylene glycol 1450 is preferred and included in a concentration of 1% (w/v) in the formulation (for a list of typical ingredients see Table 12).

Liposomes, in addition to the excipients listed above, also optimally contained 1 mole percent of vitamin E or dl α-tocopherol as an antioxidant. This protects the unsaturated fatty acid moieties in the surfactants from oxidation, which in turn could catalyze the antigen degradation. Liposomes thus formulated are mixed with emulsions in different ratios e.g. 1:10 to 10:1 (v/v) as discussed earlier, even though for convenience 1:1 (v/v) is preferred. This mixture contains adequate amounts of the antigens and the immunostimulant in a therapeutic dose.

A number of other techniques can be used to prepare the desired compositions. For example, Gauthier and Levinson (EP0211257) freeze-dried a phospholipid emulsion in a two step process: the first step comprised spray freezing i.e., spraying a pre-formed emulsion onto a chlorofluorocarbon or similar compatible solvent at $\leq -20°$ C. and collecting the frozen particles (which already contained cryoprotectants) and in a second step lyophilizing the particles. The resultant powder or cake, which generally contained sugars in vast excess, rehydrated to generate oil-in-water emulsions with particle sizes in the range of 0.48–0.7 micron. This method is cumbersome, provides large emulsion drops which may not be useful for certain therapeutic applications, where, for example, one would expect the particles to reside at the site of injection and slowly drain into lymphatics or suitable anatomic sites. Thus, one aspect of the current invention is to generate small, submicron liposome ($\leq 0.4\mu$) and emulsion particles in a suitable medium providing storage advantage such that the size could be maintained without further growth. Another aspect of the invention is to prepare lyophilized liposome/emulsion combinations that are readily reconstitutable to particles with a mean diameter $\leq 0.4$; suitable for intended applications as vaccines.

The following illustrates by way of example the different dosage forms of antigen-bearing liposome/emulsion combinations as being useful as vaccines providing higher immunogenicity in the animals as demonstrated above.

1. Liquid antigen-bearing liposome/emulsion combination

Liposomes are prepared in sucrose-citrate (10% w/v, 10 mM) or any other combination of excipients discussed in this section with the antigen. Any unbound protein is removed by a suitable technique such as dialysis, diafiltration or centrifugation (preferably centrifugation). The liposomes are suspended in the medium containing the same excipients as the interior of the liposomes except the antigen. In another set of liposomes (though not preferred), the vesicles are prepared in saline (0.9% w/v) or PBS together with the antigens and, after washing to remove unbound protein the liposomes are suspended in the cryoprotectant/ viscosity enhancer and buffer, e.g. sucrose, PEG 1450, or citrate. Emulsions which are typically processed by homogenization in water were adjusted to physiologic osmolality with the excipient combinations to match the liposomes. Equal volumes of the vesicles and emulsions are combined and stored in a refrigerator at 2°–8° C. Analysis over time indicates no loss of liposomal contents and retention of size by both particles (liposomes and emulsions).

2. Frozen antigen-bearing liposomes/emulsion combination

Liposomes (fusogenic or otherwise) are prepared in sucrose (8% w/v)/mannitol (1% w/v), phosphate 10 mM/PEG 1450 (1% w/v) containing the protein antigen and extruded through a polycarbonate filter to reduce the average particle size to 0.1–0.4μ. Excess antigen is removed by centrifugation, and pelleted vesicles are resuspended in the same buffer excipient mixture. The liposomes are then combined with the microfluidized emulsions ($\leq 0.4\mu$) and frozen in a refrigerator to temperatures $\leq -10°$ C. After storage overnight, the formulation is allowed to thaw slowly to ambient temperature. Alternatively, liposomes and emulsions are frozen separately, thawed, and mixed or liposomes at 2°–8° C. are mixed with emulsions treated by freeze-thaw and combined prior to administration in animals. Both particulate materials retain their physical integrity during the freeze-thaw cycle. They are thus expected to provide storage convenience for human administration by being stored in single-vial or two-vial packages. It is found that certain saccharides (e.g. mannitol, lactose) included as the sole cryoprotectants do not help preserve the physical structure of liposomes and emulsions. However, cryoprotectants such as glycerol (2–20% w/v, preferably 2%), proline (0.3M), arginine (0.3M), sucrose-mannitol (sucrose 8% w/v, mannitol 1% w/v), sucrose-gly or arginine (sucrose 8% w/v, glycine or arginine 60 mM), mixtures of amino acids (proline, glycine, alanine; 100 mM each) all provide adequate cryoprotection during the freeze-thaw process, suggesting the possible application in vaccine formulations.

Liposomes containing antigens and excipients such as PBS, saline or phosphate in the interior and cryoprotectant/buffer/ (viscosity enhancer) in the exterior phase could also be mixed with the emulsion in the same cryoprotectant combination for the intended application.

3. Lyophilized antigen-bearing liposomes/emulsion combinations

As a stable storage form, this combination is highly preferred because bulk water which could cause chemical instability to lipids and proteins is eliminated. In addition, carbohydrates and amino acids commonly used as cryoprotectants are good support media for microbial growth. The following is illustrative of the design used in lyophilizations to generate dried vaccine formulations.

Antigen-bearing liposomes suspended in suitable cryoprotectant/buffer/(viscosity enhancer) such as those listed in Table 12 are combined with microfluidized emulsions in the same medium and freeze dried at temperatures below the cake collapse temperature for that excipient combination for 24–72 hr. (preferably 24 hr.). In one embodiment, for example, containing sucrose 10% w/v, citrate 10 mM, primary drying is initiated at −40° C. and temperature gradually raised to −10° C. under good vacuum (10–100 microns, preferably 50 microns). After the completion of the primary drying process, the shelf temperature is gradually raised to ambient temperature (10°–20° C. per hour) and left at this temperature and vacuum for an additional 2–10 hours (preferably 4 hours) or until the moisture level in the dried product is reduced to 1–3%. Another variant of this formula consists of drying liposomes and emulsions separately and mixing the reconstituted suspensions to provide the desired formulation. In either case, the lyophilized cakes have acceptable physical appearance and readily reconstitute to provide injectable vaccine formulations.

Lyophilized single- or two-vial formulations by virtue of the low water content have acceptable stabilities for the lipid components and the protein antigens. The formulations can be stored at 2°–8° C. or ambient temperatures.

TABLE 12

Combinations of Cryoprotectants and Viscosity Enhancers used in the Formulations+

Sucrose* (10% w/v)
Sucrose (6% w/v), mannitol (1% w/v)
Dextrose (5% w/v)
Sucrose (9% w/v), PEG 400, 1450 or 3350 (1% w/v)
Sucrose (9% w/v), hydrolyzed gelatin (1% w/v)
Sucrose (9% w/v), gelatin (fish skin, bovine or porcine 1% w/v)
Sucrose (9% w/v), Povidone 16000 or 40000 (1% w/v)
Glycine, alanine or proline (0.3 M pH 6–6.5)
Sucrose 9% (w/v) carboxymethyl cellulose (1% w/v) glycerol (2–20% w/v)

+In addition, phosphate or citrate buffer is used in 10 mM concentration to provide stability to antigens.
*Other sugars, such as lactose, trehalose, maltose, etc., are substituted in appropriate weight amounts to provide equivalent physiologic osmolality.

All publications and patent applications cited in this specification are herein incorporated by reference as if each individual publication or patent application were specifically and individually indicated to be incorporated by reference at the location where cited.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A vaccine composition, comprising:
   (1) an immunostimulating amount of an antigenic substance in association with liposomes, wherein the liposomes have a net negative charge; and
   (2) an oil-in-water emulsion comprising a metabolizable oil in a continuous phase surrounding said liposomes, said emulsion being present in an amount sufficient to increase immune responce relative to that of said antigenic substance and liposomes in the absence of said emulsion.

2. The composition of claim 1, wherein said antigenic substance is also present in said continuous phase in an immunostimulating amount.

3. The composition of claim 1, wherein said liposomes comprise fusogenic liposomes.

4. The composition of claim 1, wherein said liposomes and said emulsion are present in a volume ratio of from 1:10 to 10:1.

5. The composition of claim 1, wherein said liposomes and oil droplets present in said emulsion are present as particles of substantially the same size distribution range.

6. The composition of claim 5, wherein substantially all of said particles are less than 1 micron in diameter.

7. The composition of claim 1, wherein said oil-in-water emulsion further contains an immunostimulating amount of a muramyl peptide.

8. The composition of claim 7, wherein said muramyl peptide is a compound of the formula

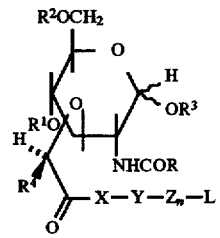

wherein R is H or COCH$_3$;

R$^1$, R$^2$, and R$^3$ independently represent H or a lipid moiety;

R$^4$ is hydrogen or alkyl;

X and Z independently represent an aminoacyl moiety selected from the group consisting of alanyl, valyl, leucyl, isoleucyl, α-aminobutyryl, threonyl, methionyl, cysteinyl, glutamyl, isoglutamyl, glutaminyl, isoglutaminyl, aspartyl, phenylalanyl, tyrosyl, tryptophanyl, lysyl, ornithinyl, arginyl, histidyl, asparinginyl, prolyl, hydroxypropyl, seryl, and glycyl;

n is 0 or 1;

Y is —NHCHR$^5$CH$_2$CH$_2$CO—, wherein R$^5$ represents an optionally esterified or amidated carboxyl group; and L is OH, NR$^6$R$^7$ where R$^6$ and R$^7$ independently represent H or a lower alkyl group, or a lipid moiety.

9. The composition of claim 8, wherein said muramyl peptide is either a muramyl dipeptide or muramyl tripeptide.

10. The composition of claim 9, wherein said muramyl peptide is selected from the group consisting of muramyl dipeptides and tripeptides linked to a phospholipid moiety through a hydroxyalkylamine moiety.

11. The composition of claim 9, wherein said muramyl peptide is N-acetylmuramyl-L-alanyl-D-isoglutaminyl-L-alanine-2-(1,2-dipalmitoyl-sn-glycero-3-(hydroxyphosphoryloxy))ethylamide.

12. The composition of claim 1, wherein said oil is an animal oil.

13. The composition of claim 12, wherein said oil is squalene.

14. The composition of claim 1, wherein said composition comprises up to 15% by volume of said oil.

15. The composition of claim 1, wherein said composition further comprises an additional emulsifying agent.

16. The composition of claim 15, wherein said additional emulsifying agent is selected from the group consisting of sorbitan esters, polyoxyethylene sorbitan mono-, di-, or triesters, polyoxyethylene fatty acids, polyoxyethylene fatty acid ethers, and combinations thereof.

17. The composition of claim 15, wherein said additional emulsifying agent is selected from the group of polyoxyethylene sorbitan 20 monooleate, Span 85 sorbitan trioleate, and combinations thereof.

18. The composition of claim 15, wherein said composition comprises up to 2.5% by weight of said additional emulsifying agent.

19. The composition of claim 1, wherein said antigenic substance is a viral particle or subunit.

20. The composition of claim 1, wherein said antigenic substance is a virus molecular antigen.

21. The composition of claim 1, wherein said antigenic substance is selected from the group of proteins consisting of HSV gD2, HIV gp120, HSV gB2, CMV gB, HCV protein and influenza vaccine antigens.

22. A method of stimulating an immune response in a host animal, comprising:

administering an effective amount of a protective antigen to said animal in association with liposomes wherein the liposomes have a net negative charge, wherein said liposomes and said antigen or antigens are administered in admixture with a continuous aqueous phase containing an oil-in-water emulsion, wherein said oil in said emulsion is a metabolizable oil and said emulsion is present in an amount sufficient to increase immune response relative to that of said antigen and liposomes in the absence of said emulsion.

23. The method of claim 22, wherein said antigen is selected from the group of proteins consisting of HSV gD2, HIV gp120, HSV gB2, CMV gB, HCV proteins and influenza vaccine antigens.

24. The method of claim 22, wherein said oil-in-water emulsion further contains an immunostimulating amount of a muramyl peptide.

25. The method of claim 22, wherein said antigenic substance is also present in said continuous phase.

26. The method of claim 22, wherein said liposomes comprise fusogenic liposomes.

27. The method of claim 22, wherein said liposomes and said emulsion are present in a volume ratio of from 1:10 to 10:1.

28. The method of claim 22, wherein said liposomes and oil droplets present in said emulsion are present as particles of substantially the same size distribution range.

29. The method of claim 28, wherein said particles are substantially all less than 1 micron in diameter.

30. The method of claim 24, wherein said muramyl peptide is a compound of the formula

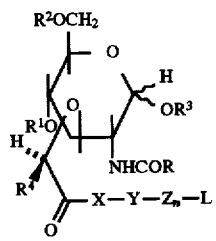

wherein R is H or COCH$_3$;

R$^1$, R$^2$, and R$^3$ independently represent H or a lipid moiety;

R$^4$ is hydrogen or alkyl;

X and Z independently represent an aminoacyl moiety selected from the group consisting of alanyl, valyl, leucyl, isoleucyl, α-aminobutyryl, threonyl, methionyl, cysteinyl, glutamyl, isoglytamyl, glutaminyl, isoglutaminyl, aspartyl, phenylalanyl, tyrosyl, tryptophanyl, lysyl, ornithinyl, arginyl, histidyl, asparinginyl, prolyl, hydroxypropyl, seryl, and glycyl;

n is 0 or 1;

Y is —NHCHR$^5$CH$_2$CH$_2$CO—, wherein R$^5$ represents an optionally esterified or amidated carboxyl group; and L is OH, NR$^6$R$^7$ where R$^6$ and R$^7$ independently represent H or a lower alkyl group, or a lipid moiety.

31. The method of claim 30, wherein said muramyl peptide is either a muramyl dipeptide or muramyl tripeptide or a mixture thereof.

32. The method of claim 31, wherein said muramyl peptide comprises a member selected from the group consisting of muramyl dipeptides and tripeptides linked to a phospholipid moiety through a hydroxyalkylamine moiety.

33. The method of claim 32, wherein said muramyl peptide is N-acetylmuramyl-L-alanyl-D-isoglutaminyl-L-alanine- 2-(1,2-dipalmitoyl-sn-glycero-3-(hydroxyphosphorloxy))ethylamide.

34. The method of claim 33, wherein said oil is squalane.

35. The method of claim 22, wherein said oil is squalane.

36. The method of claim 22, wherein said continuous aqueous phase further comprises an additional emulsifying agent.

37. The method of claim 36, wherein said additional emulsifying agent comprises a member selected from the group consisting of sorbitan esters, polyoxyethylene sorbitan mono-, di-, or triesters, polyoxyethylene fatty acids, polyoxyethylene fatty acid ethers, and combinations thereof.

* * * * *